US009655993B2

(12) United States Patent
Kaplan et al.

(10) Patent No.: US 9,655,993 B2
(45) Date of Patent: *May 23, 2017

(54) TISSUE-ENGINEERED SILK ORGANS

(71) Applicant: Trustees of Tufts College, Medford, MA (US)

(72) Inventors: David L. Kaplan, Concord, MA (US); Fiorenzo Omenetto, Wakefield, MA (US); Jeffrey K. Marchant, Littleton, MA (US); Noorjahan Panjwani, Medford, MA (US); Brian Lawrence, Minneapolis, MN (US)

(73) Assignee: Trustees of Tufts College, Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/793,464

(22) Filed: Jul. 7, 2015

(65) Prior Publication Data

US 2016/0151538 A1    Jun. 2, 2016

Related U.S. Application Data

(62) Division of application No. 12/528,634, filed as application No. PCT/US2008/055072 on Feb. 27, 2008, now Pat. No. 9,102,916.

(60) Provisional application No. 60/973,023, filed on Sep. 17, 2007, provisional application No. 60/903,800, filed on Feb. 27, 2007.

(51) Int. Cl.
| | | |
|---|---|---|
| *A01N 1/02* | (2006.01) |
| *A61L 27/36* | (2006.01) |
| *A61L 27/22* | (2006.01) |
| *A61L 27/38* | (2006.01) |
| *A61L 27/56* | (2006.01) |
| *C12N 5/00* | (2006.01) |
| *C12N 5/079* | (2010.01) |
| *G01N 33/50* | (2006.01) |

(52) U.S. Cl.
CPC ......... *A61L 27/3604* (2013.01); *A61L 27/225* (2013.01); *A61L 27/227* (2013.01); *A61L 27/3804* (2013.01); *A61L 27/3839* (2013.01); *A61L 27/3891* (2013.01); *A61L 27/56* (2013.01); *C12N 5/0068* (2013.01); *C12N 5/0621* (2013.01); *G01N 33/5044* (2013.01); *A61L 2300/412* (2013.01); *C12N 2533/50* (2013.01)

(58) Field of Classification Search
None
See application file for complete search history.

(56) References Cited

U.S. PATENT DOCUMENTS

| | | |
|---|---|---|
| 1,989,005 A | 1/1935 | Fink et al. |
| 4,233,212 A | 11/1980 | Otoi et al. |
| 4,798,722 A | 1/1989 | Edman et al. |
| 4,806,355 A | 2/1989 | Goosen et al. |
| 4,820,418 A | 4/1989 | Hirotsu et al. |
| 5,015,476 A | 5/1991 | Cochrum et al. |
| 5,047,507 A | 9/1991 | Buchegger et al. |
| 5,093,489 A | 3/1992 | Diamantoglou |
| 5,245,012 A | 9/1993 | Lombari et al. |
| 5,263,992 A | 11/1993 | Guire |
| 5,270,419 A | 12/1993 | Domb |
| 5,290,494 A | 3/1994 | Coombes et al. |
| 5,576,881 A | 11/1996 | Doerr et al. |
| 5,606,019 A | 2/1997 | Cappello |
| 5,728,810 A | 3/1998 | Lewis et al. |
| 5,770,193 A | 6/1998 | Vacanti et al. |
| 5,902,800 A | 5/1999 | Green et al. |
| 5,932,462 A | 8/1999 | Harris et al. |
| 5,994,099 A | 11/1999 | Lewis et al. |
| 6,106,816 A | 8/2000 | Hitchen |
| 6,110,590 A | 8/2000 | Zarkoob et al. |
| 6,123,819 A | 9/2000 | Peeters |
| 6,127,143 A | 10/2000 | Gunasekaran |
| 6,175,053 B1 | 1/2001 | Tsubouchi |
| 6,245,537 B1 | 6/2001 | Williams et al. |
| 6,267,776 B1 | 7/2001 | O'Connell |
| 6,302,848 B1 | 10/2001 | Larson et al. |
| 6,310,188 B1 | 10/2001 | Mukherjee |
| 6,325,810 B1 | 12/2001 | Hamilton et al. |
| 6,337,198 B1 | 1/2002 | Levene et al. |
| 6,372,244 B1 | 4/2002 | Antanavich et al. |

(Continued)

FOREIGN PATENT DOCUMENTS

| | | |
|---|---|---|
| CA | 2405850 A1 | 10/2002 |
| EP | 0361391 A2 | 4/1990 |

(Continued)

OTHER PUBLICATIONS

Abraham, M.H. et al., Draize rabbit eye test compatibility with eye irritation thresholds in humans: a quantitative structure-activity relationship analysis, Toxicological Sciences, 76:384-391 (2003).
Agarwal et al., Effect of Moisture Absorption on the Thermal Properties of Bombyx mori Silk Fibroin Films, Journal of Applied Polymer Science, 63(3):401-410 (1997).
Alaminos, M. et al, Construction of a complete rabbit cornea substitute using a fibrin-agarose scaffold, Invest Opthamol Vis Sci, 47(8):3311-3317 (2006).
Altman, G. et al., Silk matrix for tissue engineered anterior cruciate ligaments, Biomaterials, 23:4131-4141 (2002).

(Continued)

*Primary Examiner* — Celine Qian
(74) *Attorney, Agent, or Firm* — Choate, Hall & Stewart, LLP

(57) ABSTRACT

This invention relates to a lamellae tissue layer, comprising a grooved silk fibroin substrate comprising tissue-specific cells. The silk fibroin substrates provides an excellent means of controlling and culturing cell and extracellular matrix development. A multitude of lamellae tissue layers can be used to create a tissue-engineered organ, such as a tissue-engineered cornea. The tissue-engineered organ is non-immunogenic and biocompatible.

13 Claims, 6 Drawing Sheets

(56) References Cited

U.S. PATENT DOCUMENTS

| | | |
|---|---|---|
| 6,379,690 B2 | 4/2002 | Blanchard et al. |
| 6,395,734 B1 | 5/2002 | Tang et al. |
| 6,440,740 B1 | 8/2002 | Tsubouchi et al. |
| 6,592,623 B1 | 7/2003 | Bowlin et al. |
| 6,815,427 B2 | 11/2004 | Tsubouchi et al. |
| 6,902,932 B2 | 6/2005 | Altman et al. |
| 7,041,797 B2 | 5/2006 | Vollrath |
| 7,057,023 B2 | 6/2006 | Islam et al. |
| 7,285,637 B2 | 10/2007 | Armato et al. |
| 7,635,755 B2 | 12/2009 | Kaplan et al. |
| 7,662,409 B2 | 2/2010 | Masters |
| 7,674,882 B2 | 3/2010 | Kaplan et al. |
| 7,727,575 B2 | 6/2010 | Kaplan et al. |
| 7,842,750 B2 | 11/2010 | Reezigt et al. |
| 7,842,780 B2 | 11/2010 | Kaplan et al. |
| 7,960,509 B2 | 6/2011 | Kaplan et al. |
| 8,071,722 B2 | 12/2011 | Kaplan et al. |
| 8,354,501 B2 | 1/2013 | Kaplan et al. |
| 8,501,172 B2 | 8/2013 | Kaplan et al. |
| 9,040,073 B2 | 5/2015 | Boison et al. |
| 9,068,282 B2 | 6/2015 | Cannizzaro et al. |
| 9,102,916 B2 | 8/2015 | Kaplan et al. |
| 9,504,575 B2 | 11/2016 | Kaplan et al. |
| 2002/0028243 A1 | 3/2002 | Masters |
| 2002/0081726 A1 | 6/2002 | Russell et al. |
| 2003/0007991 A1 | 1/2003 | Masters |
| 2003/0183978 A1 | 10/2003 | Asakura |
| 2004/0005363 A1 | 1/2004 | Tsukada et al. |
| 2004/0266992 A1 | 12/2004 | Migliaresi et al. |
| 2005/0147681 A1 | 7/2005 | Zhao |
| 2005/0260706 A1 | 11/2005 | Kaplan et al. |
| 2006/0273279 A1 | 12/2006 | Kaplan et al. |
| 2007/0187862 A1 | 8/2007 | Kaplan et al. |
| 2007/0212730 A1 | 9/2007 | Vepari et al. |
| 2008/0058400 A1 | 3/2008 | Yang et al. |
| 2008/0085272 A1 | 4/2008 | Kaplan et al. |
| 2008/0293919 A1 | 11/2008 | Kaplan et al. |
| 2009/0171467 A1 | 7/2009 | Mann et al. |
| 2009/0202614 A1 | 8/2009 | Kaplan et al. |
| 2009/0232963 A1 | 9/2009 | Kaplan et al. |
| 2009/0234026 A1 | 9/2009 | Kaplan et al. |
| 2009/0297588 A1 | 12/2009 | Rheinnecker et al. |
| 2010/0028451 A1 | 2/2010 | Kaplan et al. |
| 2010/0046902 A1 | 2/2010 | Kaplan et al. |
| 2010/0055438 A1 | 3/2010 | Kaplan et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0095827 A1 | 4/2010 | Rheinnecker et al. |
| 2010/0096763 A1 | 4/2010 | Kaplan et al. |
| 2010/0120116 A1 | 5/2010 | Kaplan et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0292338 A1 | 11/2010 | Rheinnecker et al. |
| 2011/0046686 A1 | 2/2011 | Kaplan et al. |
| 2011/0076384 A1 | 3/2011 | Cannizzaro et al. |
| 2011/0105402 A1 | 5/2011 | Kim et al. |
| 2011/0121485 A1 | 5/2011 | Rheinnecker et al. |
| 2011/0135697 A1 | 6/2011 | Omenetto et al. |
| 2011/0152214 A1 | 6/2011 | Boison et al. |
| 2011/0171239 A1 | 7/2011 | Kaplan et al. |
| 2012/0121820 A1 | 5/2012 | Kaplan et al. |
| 2012/0123519 A1 | 5/2012 | Lovett et al. |
| 2012/0171770 A1 | 7/2012 | Numata et al. |
| 2012/0231499 A1 | 9/2012 | Lee et al. |
| 2013/0039986 A1 | 2/2013 | Kaplan et al. |
| 2013/0156844 A1 | 6/2013 | Kaplan et al. |
| 2013/0287835 A1 | 10/2013 | Kaplan et al. |
| 2014/0134240 A1 | 5/2014 | Kaplan et al. |
| 2015/0231311 A1 | 8/2015 | Kaplan et al. |

FOREIGN PATENT DOCUMENTS

| | | |
|---|---|---|
| EP | 1013756 A1 | 6/2000 |
| EP | 1440088 A2 | 7/2004 |
| EP | 1602383 A1 | 12/2005 |
| GB | 1182153 A | 2/1970 |
| JP | 55-139427 | 10/1980 |
| JP | 56166235 | 12/1981 |
| JP | S58-38449 | 8/1983 |
| JP | 60-142259 | 7/1985 |
| JP | 60-295677 | 12/1985 |
| JP | H01501362 A | 5/1989 |
| JP | 01118544 | 11/1989 |
| JP | 04-263611 B2 | 9/1992 |
| JP | 4322657 A | 11/1992 |
| JP | H05-43600 A | 2/1993 |
| JP | 05163132 A | 6/1993 |
| JP | H06-346314 | 12/1994 |
| JP | 08-295697 | 11/1996 |
| JP | 10-36676 | 2/1998 |
| JP | 11-026344 | 1/1999 |
| JP | 11253155 | 9/1999 |
| JP | 2000-273264 A | 10/2000 |
| JP | 2003-192807 A | 7/2003 |
| JP | 2004-068161 A | 3/2004 |
| JP | 2006/504450 A | 2/2006 |
| WO | WO-8803785 A1 | 6/1988 |
| WO | WO-97/08315 A1 | 3/1997 |
| WO | WO-99/01089 A1 | 1/1999 |
| WO | WO-99/45964 A1 | 9/1999 |
| WO | WO-01/25403 | 4/2001 |
| WO | WO-01/36531 | 5/2001 |
| WO | WO-01/56626 A1 | 8/2001 |
| WO | WO-02/072931 | 9/2002 |
| WO | WO-03/022909 A1 | 3/2003 |
| WO | WO-03/038033 A2 | 5/2003 |
| WO | WO-04/000915 A2 | 12/2003 |
| WO | WO-2004/041845 A2 | 5/2004 |
| WO | WO-2005/012606 A2 | 2/2005 |
| WO | WO-2005/123114 A2 | 12/2005 |
| WO | WO-2008/052755 A2 | 5/2008 |
| WO | WO-2008/052775 A2 | 5/2008 |
| WO | WO-2008/127404 A2 | 10/2008 |
| WO | WO-2008/127405 A2 | 10/2008 |
| WO | WO-2009/023615 A1 | 2/2009 |
| WO | WO-2009/061823 A1 | 5/2009 |
| WO | WO-2009/100280 A2 | 8/2009 |
| WO | WO-2009/126689 A2 | 10/2009 |
| WO | WO-2009/140588 A1 | 11/2009 |
| WO | WO-2009/153140 A2 | 12/2009 |
| WO | WO-2009/155397 A2 | 12/2009 |
| WO | WO-2009/156226 A2 | 12/2009 |
| WO | WO-2010/036992 A2 | 4/2010 |
| WO | WO-2010/060600 A1 | 6/2010 |
| WO | WO-2011/006133 A2 | 1/2011 |
| WO | WO-2012/087823 A2 | 6/2012 |

OTHER PUBLICATIONS

Altman, G. et al., Silk-based biomaterials, Biomaterials, 24:401-416 (2003).

Altman, G.H. et al., Cell differentiation by mechanical stress, The FASEB Journal, 16:270-272 (2002).

Ando et al, Piezoelectric and Related properties of Hydrated Silk Fibroin, Reports on Progress in Polymer Physics in Japan, XXIII:775-778 (1980).

Asakura et al., Conformation Characterization of Bombyx Mori Silk Fibroin in the Solid State by High-Frequency 13C Cross Polarization-Magic Angle Spinning NMR, X-ray Diffraction, and Infrared Spectroscopy, Macromolecules, 18:1841-1845 (1985).

Asakura et al., NMR of silk fibroin 2. 13C NMR study of the chain dynamics and solution structure of Bombyx mori silk fibroin, Macromolecules, 17:1075-1081 (1984).

Auger, F.A. et al., A truly new approach for tissue engineering: the LOEX self-assembly technique, Ernst Schering Res Found Workshop, 35:73-88 (2002).

Bai et al., Key Engineering Materials, 342-343:229-232 (2007).

(56) References Cited

OTHER PUBLICATIONS

Berryhill, B.L. et al., Increased SPARC accumulation during corneal repair, Experimental Eye Research, 77(1):85-92 (2003).
Bettinger, C.J. et al., Silk fibroin microfluidic devices, Advanced Materials, 19(5):2847-2850 (2007).
Bini et al., Mapping Domain Structures in Silks from Insects and Spiders Related to Protein Assembly, Journal of Mol. Biol., 335:27-40 (2004).
Birk, D.E. et al., Collagen fibrillogenesis in vitro: interaction of types I and V collagen regulates fibril diameter, Journal of Cell Science, 95(4):649-657 (1990).
Birk, D.E. et al., Collagen type I and type V are present in the same fibril in the avian corneal stroma, Journal of Cell Biology, 106(3):999-1008 (1988).
Boisjoly, H.M. et al., Risk factors of corneal graft failure, Ophthalmology, 100(11):1728-1735 (1993).
Bradley, J.M.B. et al., Effects of mechanical stretching on trabecular matrix metalloproteinases, Investigative Ophthalmology and Visual Science, 42(7):1505-1513 (2001).
Breen, E.C., Mechanical strain increases type I collagen expression in pulmonary fibroblasts in vitro, Journal of Applied Physiology, 88:203-209 (2000).
Bryant, M.R. et al., Corneal tensile strength in fully healed radial keratotomy wounds, Investigative Ophthalmology and Visual Science, 35(7):3022-3031 (1994).
Cai et al., Fabrication of Chitosan/Silk Fibroin Composite Nanofibers for Wound-dressing Applications, Int. J. Mol. Sci., 11:3529-3539 (2010).
Carlsson, D.J. et al., Bioengineered corneas: how close are we? Current Opinion in Ophthalmology, 14(4):192-197 (2003).
Chaloin-Dufau, C. et al., Appearance of the keratin pair K3/K12 during embryonic and adult corneal epithelial differentiation in the chick and in the rabbit, Cell Differentiation and Development, 32(2):97-108 (1990).
Chen et al., Conformation transition kinetics of Bombyx mori silk protein, Proteins: Structure, Function, and Bioinformatics, 68:223-231 (2007).
Chen et al., Human bone marrow stromal cell and ligament fibroblast responses on RGD-modified silk fibers, J Biomed Mater Res, 67A:559-570 (2003).
Chen et al., pH sensitivity and ion sensitivity of hydrogels based on complex-forming chitosan/silk fibroin interpenetrating polymer network, J. Appl. Polymer Sci., 65:2257-62 (1997).
Chen et al., Separation of alcohol-water mixture by pervaporation through a novel natural polymer blend membrane-chitosan/silk fibroin blend membrane—chitosan / silk fibroin blend membrane, J Appl Polymer Sci, 73:975-980 (1999).
Chiquet, M. et al., Regulation of extracellular matrix synthesis by mechanical stress, Biochemistry and Cell Biology, 74(6):737-744 (1996).
Cintron, C. et al., Morphogenesis of rabbit corneal stroma, Investigative Ophthalmology and Visual Science, 24(5):543-556 (1983).
Conn, A. et al., Delivery of pCMV-S DNA using the Helios gene gun system is superior to intramuscular injection in Balb/c mice, Gene Transfer, Bio-Rad Laboratories, Inc. Bulletin, 2726:1-4 (1999).
Cunniff, P.M. et al., Mechanical and thermal properties of dragline silk from the spider Nephila clavipes, Polymers for Advanced Technologies, 5:401-410 (1994).
Dal Pra, I. et al., De novo engineering of reticular connective tissue in vivo by silk fibroin nonwoven materials, Biomaterials, 26(14):1987-1999 (2005).
Dalby, M.J. et al., Nucleus alignment and cell signaling in fibroblasts: response to a micro-grooved topography, Experimental Cell Research, 284(2):274-282 (2003).
Demura et al., Immobilization of biocatalysts with Bombyx mori silk fibroin by several kinds of physical treatment and its application to glucose sensors, Biosensors, 4:361-372 (1989).
Demura et al., Porous membrane of Bombyx mori silk fibroin: structure characterization, physical properties and application to glucose oxidase immobilization, Journal of Membrane Science, 59:39-52 (1991).
Den Braber, E.T. et al., Orientation of ECM protein deposition, fibroblast cytoskeleton, and attachment complex components on silicone microgrooved surfaces, Journal of Biomedical Materials Research, 40(2),291-300 (1998).
Derwent Record, Production of aqueous solution of silk fibroin at high concentration, Abstract of JP 08295697 A2, Nov. 12, 1996.
Doane, K.J. et al., Collagen fibril assembly by corneal fibroblasts in three-dimensional collagen gel cultures: small-diameter heterotypic fibrils are deposited in the absence of keratan sulfate proteoglycan, Experimental Cell Research, 202:113-124 (1992).
Donohue, D.et al., Numerical modeling of the cornea's lamellar structure and birefringence properties, Journal of Optical Society of America, 12(7):1425-1438 (1995).
Doshi et al. Electrospinning process and applications of electrospun fibers, Journal of Electrostatics, 35:151-160 (1995).
Dunn, GA et al., Alignment of fibroblasts on grooved surfaces described by a simple geometric transformation, Journal of Cell Sci, 83:313-340 (1986).
Eastwood, M. et al., Effect of precise mechanical loading on fibroblast populated collagen lattices: morphological changes, Cell Motility and the Cytoskeleton, 40:13-21 (1998).
Ethier, C.R. et al., Ocular biomechanics and biotransport, Annual Review of Biomedical Engineering, 6:249-273 (2004).
Fini, M. et al., The healing of confined critical size cancellous defects in the presence of silk fibroin hydrogel, Biomaterials, 26(17):3527-3536 (2005).
Franks, T., EU bans animal testing for cosmetics, BBC News, 1:1 (2003).
Freddi et al., Silk fibroin/cellulose blend films: preparation, structure, and physical properties, Journal of Appl Polymer Sci, 56:1537-1545 (1995).
Fuchs, S. et al., Outgrowth endothelial cells isolated and expanded from human peripheral blood progenitor cells as a potential source of autologous cells for endothelialization of silk fibroin biomaterials, Biomaterials, 27(31):5399-5408 (2006).
Furst et al., Release of Glutaraldehyde From an Albumin-Glutaraldehyde.
Garate, M. et al., In vitro pathogenicity of Acanthamoeba is associated with the expression of the mannose-binding protein, Investigative Ophthalmology and Visual Science, 47(3):1056-1062 (2006).
Gaudreault, M. et al., Influence of Sp1/Sp3 expression on corneal epithelial cells proliferation and differentiation properties in reconstructed tissues, Investigative Ophthalmology and Visual Science, 44(4):1447-1457 (2003).
Gill et al., Improved Hemostasis During Laparoscopic Partial Nephrectomy Using Gelatin Matrix Thrombin Sealant, Urology, 65:463-466 (2005).
Gipson, I.K. et al., Hemidesmosomes and anchoring fibril collagen appear synchronously during development and wound healing, Developmental Biology, 126(2):253-262 (1988).
Gobin, AS, et al., Journal of Biomedical Materials Research, Part A, Structural and mechanical characteristics of silk fibro n and chitosan blend scaffolds for tissue regeneration, 74A(3):465-473 (2005).
Gordon, M.K. et al., Temporal expression of types XII and XIV collagen mRNA and protein during avian corneal development, Developmental Dynamics, 206:49-58 (1996).
Gosline, J.M. et al., The structure and properties of spider silk, Endeavour, 10:37-43 (1986).
Hijirida et al., 13C NMR of Nephila clavipes major ampullate silk gland, Biophysical Journal, 71:3442-3447 (1996).
Hinman et al., Synthetic spider silk: a modular fiber, TIBTECH, 18:374-379 (2000).
Hofmann, S. et al., Silk fibroin as an organic polymer for controlled drug delivery, Journal of Controlled Release, 111:219-227 (2006).
Horan et al., In vitro degradation of silk fibroin, Biomaterials, 26:3385-3393 (2005).

(56) References Cited

OTHER PUBLICATIONS

Hu et al., Regulation of Silk Material Structure by Temperature-Controlled Water Vapor Annealing, Biomacromolecules, 12:1686-1696 (2011).
Hu, X. et al., Tissue engineering of nearly transparent corneal stroma, Tissue Engineering, 11(11-12):1710-1717 (2005).
Huang et al., Generation of synthetic elastin-mimetic small diameter fibers and fiber networks, Macromolecules, 33:2989-2997 (2000).
Ingber, D.E., Tensegrity II. How structural networks influence cellular information processing networks, Journal of Cell Science, 116:1397-1408 (2003).
International Preliminary Report on Patentabilitiy for PCT/US2008/055072, 7 pages (Sep. 1, 2009).
International Search Report for PCT/US2008/055072, 4 pages (Aug. 28, 2008).
Jacobs, J. and Taravella, M., Corneal graft rejection, eMedicine, 1:1-17 (2014).
Jang et al., Restoration of peri-implant defects in immediate implant installations by Choukroun platelet-rich fibrin and silk fibroin powder combination graft, Oral Surg Oral Med Oral Pathol Oral Radiol Endod, 09:831-836 (2010).
Jenkins et al., Clinical and Experimental Observations on the Use of Gelatin Sponge, or Foam, Surgery, 20:124-132 (1946).
Jester, J.V. et al., Corneal keratocytes: in situ and in vitro organization of cytoskeletal contractile proteins, Investigative Ophthalmology and Visual Science, 35(2):730-743 (1994).
Jiang et al., Tensile behavior and morphology of differently degummed silkworm (*Bombyx mori*) cocoon silk fibres, Materials Letters, 60:919-925 (2006).
Jin et al., Biomaterial films of Bombyx mori silk fibroin with poly(ethylene oxide), Biomacromolecules, 5(3):711-717 (2004).
Jin et al., Electrospinning Bombyx mori silk with poly(ethylene oxide), Biomacromolecules, 3:1233-1239 (2002).
Jin et al., Mechanism of silk processing in insects and spiders, Nature, 424:1057-1061 (2003).
Jin et al., Water-Stable Silk Films with Reduced β-Sheet Content, Adv. Funct. Mater., 15:1241-1247 (2005).
Joyce, N.C., Proliferative capacity of the corneal endothelium, Progress in Retinal and Eye Research, 22(3):359-389 (2003).
Jumblatt, M.M. and Neufeld, A.H., Beta-adrenergic and serotonergic responsiveness of rabbit corneal epithelial cells in culture, Investigative Ophthalmology and Visual Science, 24(8):1139-1143 (1983).
Kalayoglu, M.V., In search of the artificial cornea: recent developments in keratoprostheses, OpthalmologyWeb, 1:1-2 (2006).
Kaminski, S.L. et al., Corneal sensitivity 10 years after epikeratoplasty, Journal of Refractive Surgery, 18(6):731-736 (2002).
Karageorgiou, V. et al., Bone morphogenetic protein-2 decorated fibroin films induce osteogenic differentiation of human bone marrow stromal cells, J. Biomed Mats Res., 71A:528-537 (2004).
Karring, H. et al., The human cornea proteome: bioinformatic analyses indicate import of plasma proteins into the cornea, Molecular Vision, 12:451-460 (2006).
Kawakita, T. et al., Preservation and expansion of the primate kerotocyte phenotype by downregulating TGF-beta signaling in a low-calcium, serum-free medium, Investigative Ophthalmology and Visual Science, 47(5):1918-1927 (2006).
Kim et al., Structure and Properties of Silk Hydrogels, Biomacromolecules, 5:786-792 (2004).
Kim, B.S. et al., Cyclic mechanical strain regulates the development of engineered smooth muscle tissue, Nature Biotechnology, 17(10):979-983 (1999).
Kim, J , et al., Three dimensional aqueous-derived biomaterial scaffolds from silk fibroin, Biomaterials, 26:2775-2785 (2005).
Kim, K-H et al., Journal of Biotechnology, Biological efficacy of silk fibroin nanofiber membranes for guided bone regeneration, 120(3):327-339 (2005).
Kweon et al., Preparation of semi-interpenetrating polymer networks, J Appl Polymer Sci, 80:1848-1853 (2001).
Lawrence et al., Silk film biomaterials for cornea tissue engineering, Biomaterials, 30(7):1299-1308 Author Manuscript (2009).
Lazaris, Spider silk fibers spun from soluble recombinant silk produced in mammalian cells, Science, 295:472-476 (2002).
Lee et al., A combination graft of low-molecular-weight silk fibroin with Choukroun platelet-rich fibrin for rabbit calvarial defect, Oral Surg Oral Med Oral Pathol Oral Radiol Endod, 109:e33-e38 (2010).
Leisk et al., Electrogelation for Protein Adhesives, Adv. Mater., 22:711-715 (2010).
Li, C. et al., Electrospun Silk-BMP-2 scaffolds for bone tissue engineering, Biomaterials, 27:3115-3124 (2006).
Li, F. et al., Cellular and nerve regeneration within a biosynthetic extracellular matrix for corneal transplantation, PNAS, 100(26):15346-15351 (2003).
Li, L. et al., Effect of silicon on the formation of silk fibroin/calcium phosphate composite, J Mater Sci: Mater Med, 19:577-582 (2008).
Liang et al., Improvements of the physical properties of fibroin membranes with sodium alginate, J Appl Polymer Sci, 45:1937-1943 (1992).
Lin et al., PEG Hydrogels for the Controlled Release of Biomolecules in Regenerative Medicine, Pharmaceutical Research, 26(3):631-643 (2008).
Lowe et al., Evaluation of the topical hemostatic efficacy and safety of TISSEEL VH S/D fibrin sealant compared with currently licensed TISSEEL VH in patients undergoing cardiac surgery: a phase 3, randomized double-blind clinical study, J Cardiovasc Surg, 48(3):323-331 (2007).
Lu et al., Stabilization of Enzymes in Silk Films, Biomacromolecules, 10:1032-1042 (2009).
Lu et al., Water-Insoluble Silk Films with Silk I Structure, Acta Biomater, 6(4):1380-1387 (2010).
Lucas F. et al., The silk fibroins, Advances in Protein Chemistry, 13:107-242 (1958).
Marchant, J.K. et al., Association of type XII collagen with regions of increased stability and keratocyte density in the cornea, Experimental Eye Research, 75(6):683-694 (2002).
Marchant, J.K. et al., cDNA analysis predicts a cornea-specific collagen, PNAS, 88(4):1560-1564 (1991).
Marchant, J.K. et al., Reduction of type V collagen using a dominant-negative strategy alters the regulation of fibrillogenesis and results in the loss of corneal-specific fibril morphology, Journal of Cell Biology, 135(5):1415-1426 (1996).
Marcovich et al., Comparison of 2-Octyl Cyanoacrylate Adhesive, Fibrin Glue, and Suturing for Wound Closure in the Porcine Urinary Tract, Urology, 57:806-810 (2001).
Massia, S.P. et al., Covalently immobilized laminin peptide Tyr-Ile-Gly-Ser-Arg (YIGSR) supports cell spreading and co-localization of the 67-kilodalton laminin receptor with alpha-actinin and vinculin, Journal of Biological Chemistry, 268(11):8053-8059 (1993).
Masur, S.K. et al., Myofibroblasts differentiate from fibroblasts when plated at low density, PNAS 93(9):4219-4223 (1996).
McLaughlin, J.S. et al., Type V collagen synthesis and deposition by chicken embryo corneal fibroblasts in vitro, Journal of Cell Science, 94(2):371-379 (1989).
Megeed et al., Controlled release of plasmid DNA from a genetically engineered silk-elastinlike hydrogel, Pharmaceutical Research, 19(7):954-959 (2002).
Mehta, J. S. et al., Hydroxyapatite promotes superior keratocyte adhesion and proliferation in comparison with current keratoprosthesis skirt materials, British Journal of Ophthalmology, 89(10):1356-1362 (2005).
Meinel, L. et al., Silk implants for the healing of critical size bone defects, Bone, 37(5):688-698 (2005).
Meinel, L. et al., The inflammatory responses to silk films in vitro and in vivo, Biomaterials, 26(2):147-155 (2005).
Mimura, T. et al., Cultured human corneal endothelial cell transplantation with a collagen sheet in a rabbit model, Invest Opthalmol Vis Sci, 45(9):2992-2997 (2004).
Minkowski, J.S. et al., Corneal endothelial function and structure following cryo-injury in the rabbit, Investigative Ophthalmology and Visual Science, 25(12):1416-1425 (1984).

(56) References Cited

OTHER PUBLICATIONS

Musselmann, K. et al., Maintenance of the keratocyte phenotype during cell proliferation stimulated by insulin, Journal of Biological Chemistry, 280(38):32634-32639 (2005).
Nazarov, et al., Porous 3-D Scaffolds from Regenerated Silk Fibroin, Biomacromolecules, 5:718-726 (2004).
Neidlinger-Wilke, C. et al., Cell alignment is induced by cyclic changes in cell length: studies of cells grown in cyclically stretched substrates, Journal of Orthopaedic Research, 19(2):286-293 (2001).
Nishida, K. et al., Functional bioengineered corneal epithelial sheet grafts from corneal stem cells expanded ex vivo on a temperature-responsive cell culture surface, Transplantation, 77(3):379-385 (2004).
Nishida, K., Tissue engineering of the cornea, Cornea, 22(1):S28-S34 (2003).
Nishiyama, T. et al., Type XII and XIV collagens mediate interactions between banded collagen fibers in vitro and may modulate extracellular matrix deformability, Journal of Biological Chemistry, 269(45):28193-28199 (1994).
Ottino, P. et al., PAF-induced furin and MT1-MMP expression is independent of MMP-2 activation in corneal myofibroblasts, Investigative Ophthalmology and Visual Science, 46(2):487-496 (2005).
Pandit et al., Studies on Silk Fibroin. I. Molecular Weight, Sedimentation Coefficient, Viscosity and Optical Rotation of Silk Fibroin from Carbonate-Extracted Silk Fiber, Archives of Biochemistry and Biophysics, 149:259-268 (1972).
Panilaitis, B. et al., Macrophage responses to silk, Biomaterials, 24(18):3079-3085 (2003).
Park, J., Structure and properties of water annealed silk fibroin films, Master's thesis, Tufts University (2004).
Petroll, W.M. et al., Quantitative assessment of anteroposterior keratocyte density in the normal rabbit cornea, Cornea, 14(1):3-9 (1995).
Poole, C.A. et al., Keratocyte networks visualised in the living cornea using vital dyes, Journal of Cell Science, 106:685-691 (1993).
Preul et al., Application of a hydrogel sealant improves watertight closures of duraplasty onlay grafts in a canine craniotomy model, J Neurosurg, 107:642-650 (2007).
Pritchard et al., Effect of Silk Protein Processing on Drug Delivery from Silk Films, Macromol. Biosci., 13:311-320 (2013).
Qiang, L. et al., Clotting times and tensile properties of insoluble silk fibroin films containing heparin, Polymer International, 54:1076-1081 (2005).
Rajkhowa et al., Molecular Weight and Secondary Structure Change in Eri Silk During Alkali Degumming and Powdering, Journal of Applied Polymer Science, 119:1339-1347 (2011).
Raymond, G.M. et al., Rabbit corneal endothelial cells in vitro: effects of EGF, Investigative Ophthalmology and Visual Science, 27(4):474-479 (1986).
Reneker et al., Nanometre diameter fibres of polymer, produced by electrospinning, Nanotechnology, 7:216-223 (1996).
Sawyer et al., Dextran therapy in thrombophlebitis, Abstract, JAMA, 191(9):740-742 (1965).
Shimizu, T. et al., Cell sheet engineering for myocardial tissue reconstruction Biomaterials, 24:2309-2316 (2003).
Shyy, J.Y. and Chien, S., Role of integrins in cellular responses to mechanical stress and adhesion, Current Opinion in Cell Biology, 9(5):707-713 (1997).
Silva et al., Genipin-Modified Silk Fibroin Nanometric Nets, Macromol. Biosci., 8:000-000 (2008).
Soffer et al., Silk-Based Electrospun Tubular Scaffolds for Tissue Engineered Vascular Grafts, J Biomater Sci Polym Ed., 19(5):653-664 Author Manuscript (2008).
Sofia et al., Functionalized silk-based biomaterials for bone formation, Journal of Biomedical Materials Research, 54(1):139-148 (2001).
Sokolnicki, A.M. et al., Permeability of bacterial cellulose membranes, Journal of Membrane Science, 272:15-27 (2006).
Spotnitz et al., Hemostats, sealants, and adhesives: components of the surgical toolbox, Transfusion, 48:1502-1516 (2008).
Stark, H.J. et al., Organotypic cocultures as skin equivalents: A complex and sophisticated in vitro system, Biological Procedures Online, 6(1):55-60 (2004).
Steele, C., Corneal wound healing: a review, Optometry Today, 9:28-32 (1999).
Sumide et al., The FASEB Journal, 20(2):392-394 (2006).
Sung, H.J. et al., The effect of scaffold degradation rate on three-dimensional cell growth and angiogenesis, Biomaterials, 25(26):5735-5742 (2004).
Torchiana, Polyethylene Glycol Based Synthetic Sealants: Potential Uses in Cardiac Surgery, J Card Surg, 18:504-506 (2003).
Trachslin, J. et al., Rapid and reversible regulation of collagen XII expression by changes in tensile stress, Experimental Cell Research, 247(2):320-328 (1999).
Tsukada et al., Preparation and Application of Porous Silk, Fibroin Materials, J. of Applied Polymer Science, 54(4):507-514 (1994).
Unger, R.E. et al., Endothelialization of a non-woven silk fibroin net for use in tissue engineering growth and gene regulation of human endothelial cells, 25(21):5137-5146 (2004).
U.S. Appl. No. 61/224,618, filed Jul. 10, 2009 by Numata et al.
Van Den Berg, T.J. and Tan, K.E., Light transmittance of the human cornea from 320 to 700 nm for different ages, Vision Research, 34(11):1453-1456 (1994).
Vanderhooft et al., Synthesis and Characterization of Novel Thiol-Reactive Poly(ethylene glycol) Cross-Linkers for Extracellular-Matrix-Mimetic Biomaterials, Biomacromolecules, 8:2883-2889 (2007).
Vernon et al., Microgrooved fibrillar collagen membranes as scaffolds for cell support and alignment, Biomaterials, 26(16):3131-3140 (2005).
Walboomers, X.F. et al., Attachment of fibroblasts on smooth and microgrooved polystyrene, Journal of Biomedical Material Research, 46:212-220 (1999).
Wallace et al., A Tissue Sealant Based on Reactive Multifunctional Polyethylene Glycol, J Biomed Mater Res (Appl Biomater), 58:545-555 (2001).
Wang et al., Cell orientation determines the alignment of cell-produced collagenous matrix, Journal of Biomech., 36(1):97-102 (2003).
Wang et al., Growth Factor Gradients via Microsphere Delivery in Biopolymer Scaffolds for Osteochondral Tissue Engineering, J Control Release, 134(2):81-90 (2009).
Wang et al., Stem cell-based tissue engineering with silk biomaterials, Biomaterials, 27(36):6064-6082 (2006).
Wang, X. et al., Biomaterial coatings by stepwise deposition of silk fibroin, Langmuir, 21(24):11335-11341 (2005).
Wang, Y. et al., Cartilage tissue engineering with silk scaffolds and human articular chondrocytes, Biomaterials, 27:4434-4442 (2006).
Wenk et al., Silk Fibroin as a Vehicle for Drug Delivery in Tissue Regeneration, Diss. Eth No. 18659 (2009).
Wessel, H. et al., Type XII collagen contributes to diversities in human corneal and limbal extracellular matrices, Investigative Ophthalmology and Visual Science, 38(11):2408-2422 (1997).
Wheat et al., Advances in Bioadhesives, Tissue Sealants, and Hemostatic Agents, Urol Clin North Am., 36(2):265-275 (2009).
Wilkinson, C.D., Making structures for cell engineering, European Cells and Materials, 8:21-26 (2004).
Wilson et al., Surface organization and nanopatterning of collagen by dip-pen nanolithography, PNAS, 98(24):13660-13664 (2001).
Wilson, D. et al., Conformational transitions in model silk peptides, Biophysical Journal, 78(5):2690-2701 (2000).
Wilson, S.E. et al., Corneal cells: chatty in development, homeostasis, wound healing, and disease, American Journal of Ophthalmology, 136(3):530-536 (2003).
Wray et al., Effect of Processing on silk based biomaterials: Reproducibility and biocompatibility, J Biomed Mater Res Part B, 99B:89-101 (2011).
Written Opinion for PCT/US2008/055072, 6 pages (Aug. 28, 2008).
Yamada et al., AFM observation of silk fibroin on mica substrates: morphologies reflecting the secondary structures, Thin Solid Films, 440:208-216 (2003).

(56) References Cited

OTHER PUBLICATIONS

Yamada et al., Preparation of undegraded native molecular fibroin solution from silkworm cocoons, Materials Science and Engineering C, 14:41-46 (2001).

Yang, J. et al., Cell sheet engineering: recreating tissues without biodegradable scaffolds, Biomaterials, 26(33):6415-6422 (2005).

Yang, Y. et al., Biocompatibility evaluation of silk fibroin with peripheral nerve tissues and cells in vitro, Biomaterials, 28(9):1643-1652 (2007).

Yucel et al., Non-equilibrium Silk Fibroin Adhesives, J. Struct Biol., 170(2):406-412 (2010).

Zhou et al., Preparation of a novel core-shell nanostructured gold colloid-silk fibroin bioconjugate by the protein in situ redox technique at room temperature, Chem Commun, 2518-2519 (2001).

Zhou, C.Z. et al., Silk fibroin: structural implications of a remarkable amino acid sequence, Proteins: Structure, Function, and Genetics, 44(2):119-122 (2001).

Huang et al., Engineered collagen-PEO nanofibers and fabrics, J Biomater Sci Polymer Edn, 12(9):979-993 (2001).

Panjwani, N., Cornea and sclera, Chapman & Hall, Chapter 2:16-51 (1997).

Petrini et al., Silk fibroin-polyurethane scaffolds for tissue engineering, Journal of Materials Science: Materials in Medicine, 12:849-853 (2001).

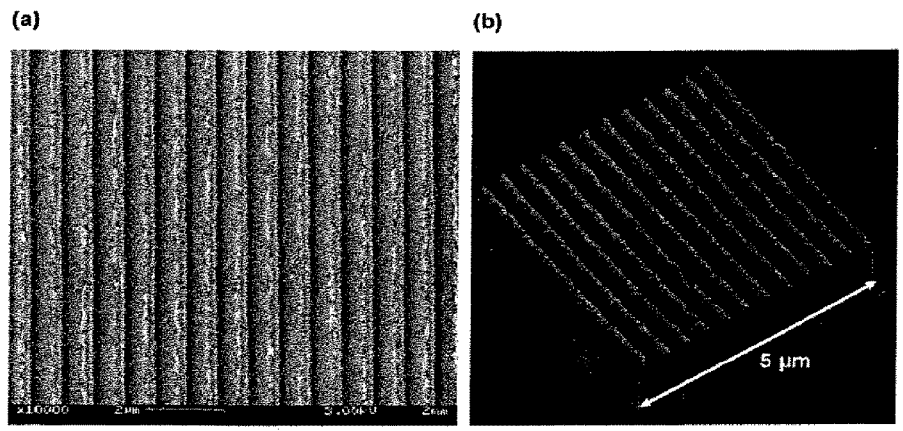

Figure 1. Silk films with cast microgrooves. (a) FESEM image of groove topology. (b) AFM of film surface. Each groove is approximately 1.7 um in width and 1 um in depth.

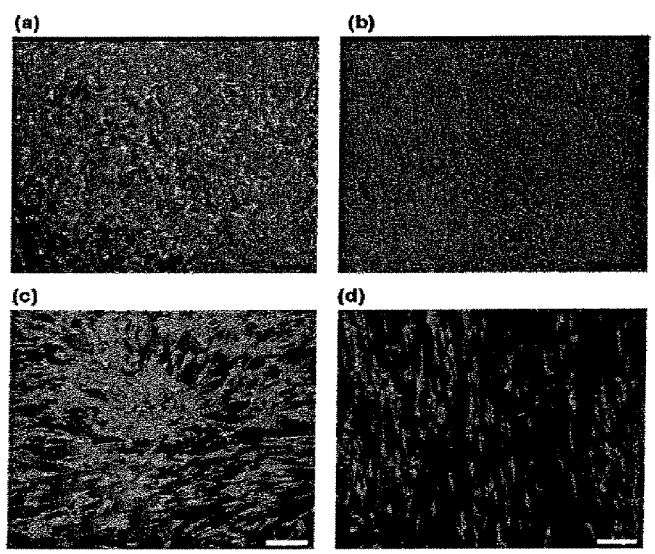

Figure 2. Aligned corneal fibroblasts cells cultured upon grooved silk lamellae substrates. (a) Transmission and (c) false color confocal images of GFP labeled corneal fibroblasts growing on non-patterned silk films. (b) Transmission and (d) false color confocal images of GFP labeled corneal fibroblasts growing on groove patterned silk lamellae surface. Scale bar is 100 um.

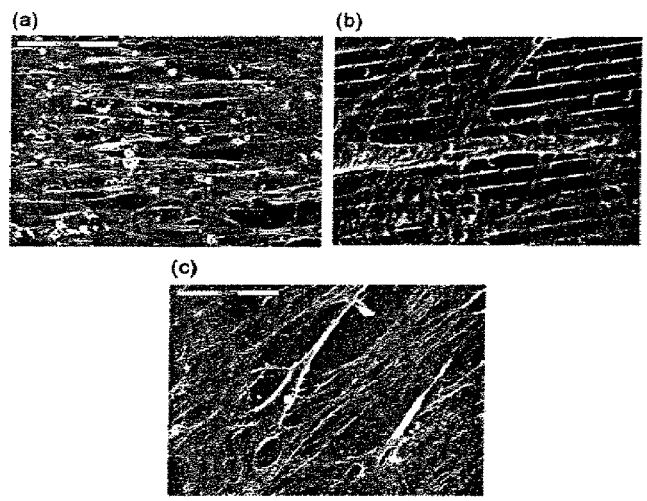
Figure 3. SEM images of aligned fibroblasts corneal cells and ECM on grooved silk lamellae constructs. (a) (c) Fibroblasts and ECM aligning on grooved silk lamellae. (b) Magnified image of aligned cell process and clear image of patterned groove geometry upon the silk lamellae.

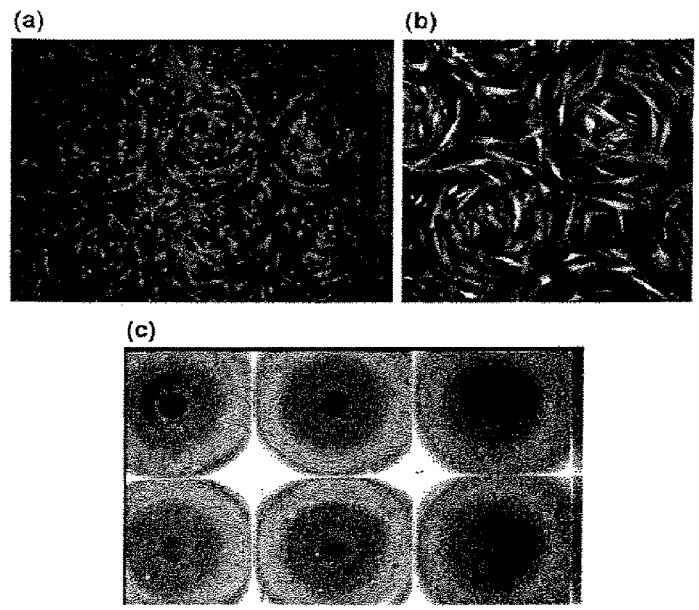

Figure 4. Corneal fibroblasts aligned on silk films with cast circular geometrical pattern. (a) Fluorescent image of GFP labeled corneal fibroblasts grown on circular patterned silk films, and (b) digitally enhanced higher magnification image of the same. (c) Circular patterned cast for silk films.

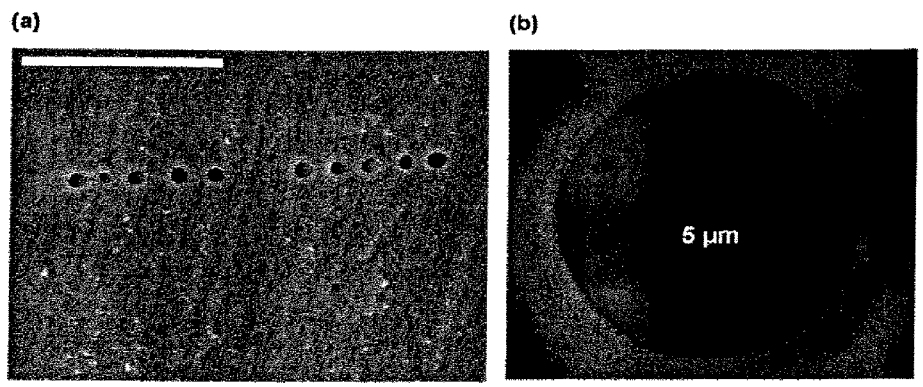

Figure 5. SEM images of laser ablated micropores in silk lamellae construct. (a) Line of micropores around 5 microns in diameter. Scale bar is 50 um. (b) High magnification image of select micropore, 5 um in diameter.

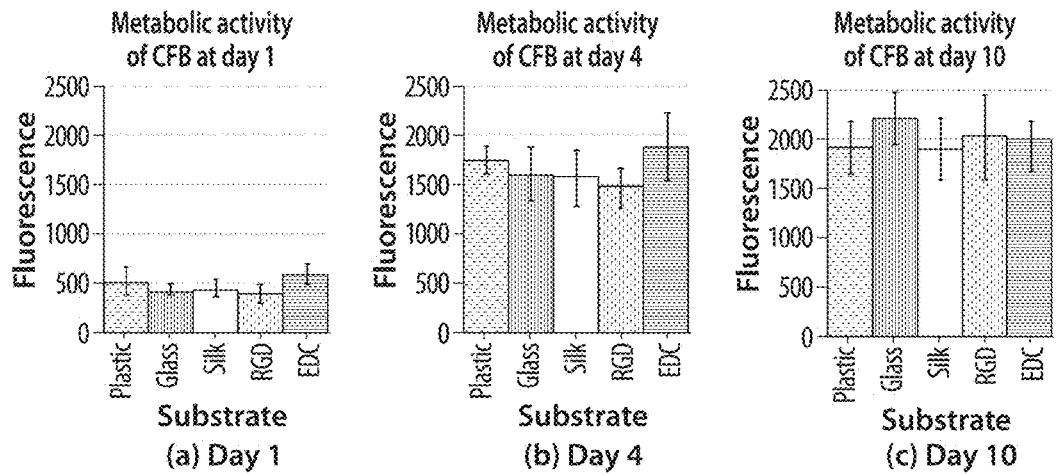

Alamar Blue metabolic assays for rabbit cornea fibroblast cultures grown on different substrates at (a) day 1, (b) day 4, and (c) day 10.

Figure 6

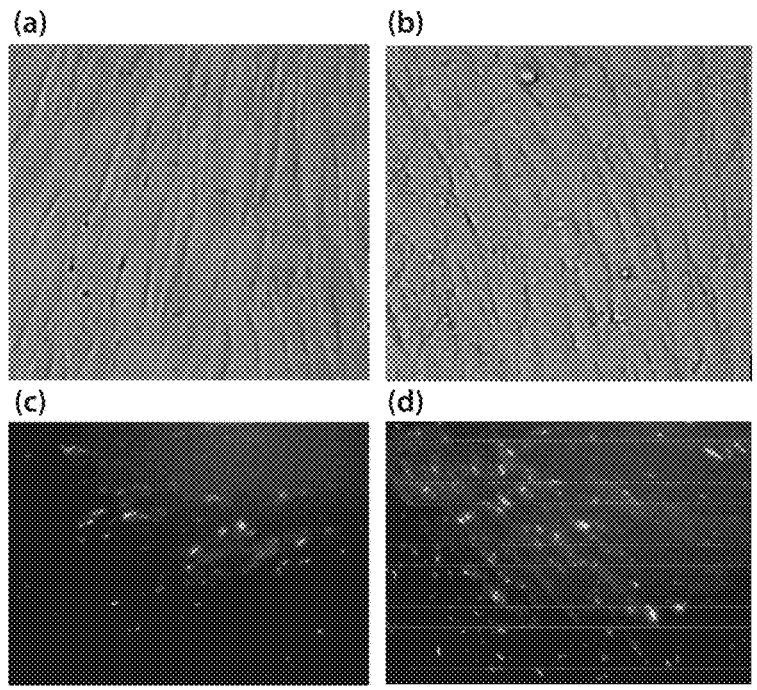

Corneal fibroblasts after 14 days in culture on:
(a) Silk coated glass and
(b) TCP. Phase contrast images, 320x. Immunofluorescent images for corneal fibroblasts on
(c) silk coated glass and
(d) glass only after four days in culture.
The green fluorescence demonstrates collagen V protein expression.

Figure 7

Transmission of light through a 30 micron silk fibroin film

Schematic of silk cornea construction

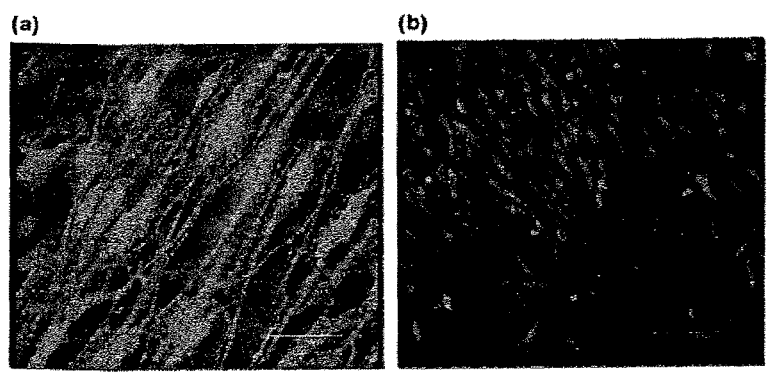
Figure 10. (a) Aligned corneal fibroblasts within the central region of the silk cornea construct. Multiple layers of cells can be seen below focus plane of cells. (b) Aligned corneal fibroblasts shown growing on grooved silk lamellae constructs.
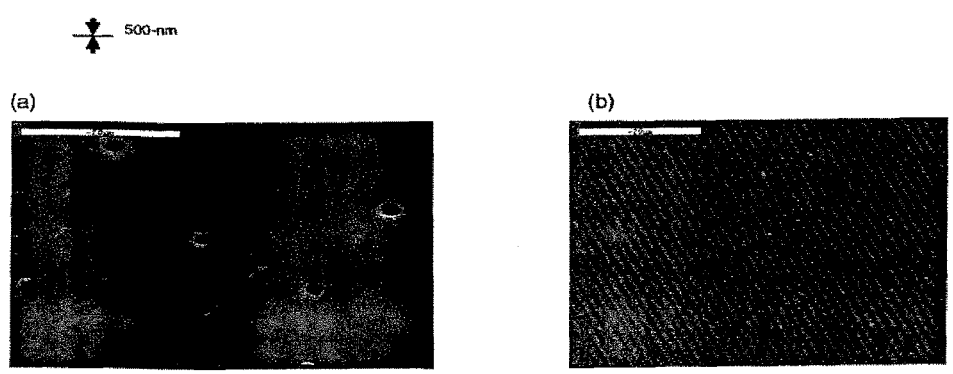
Figure 11. SEM images of silk films with (a) porous and (b) control silk films.

TISSUE-ENGINEERED SILK ORGANS

CROSS-REFERENCE TO RELATED APPLICATIONS

This application is a Continuation of U.S. patent application Ser. No. 12/528,634, filed Mar. 29, 2010, which is a 35 U.S.C. §371 National Stage of International Application No. PCT/US2008/055072 filed on Feb. 27, 2008, which designates the United States, and which claims benefit of priority under 35 U.S.C. §119(e) of U.S. Provisional Application No. 60/973,023, filed Sep. 17, 2007, and U.S. Provisional Application No. 60/903,800, filed Feb. 27, 2007, both of which are herein incorporated by reference in their entirety.

GOVERNMENT SUPPORT

This invention was supported by the NIH TERC Grant No. P41 EB002520. The Government has certain rights to the invention.

FIELD OF THE INVENTION

This invention relates to a tissue-engineered silk organs, such as tissue-engineered silk corneas, and processes used to make the tissue-engineered silk organs.

BACKGROUND

Corneal damage causes significant vision loss in the general world population, second only to cataracts, each year. Corneal replacement is a developing technology that is rapidly becoming a necessity for many patients. Many of the reasons for corneal replacement therapies include scarring from disease (e.g. herpes infection), complications from LASIK surgery, hereditary problems (e.g., Fuch's disease), and complications from other surgeries (e.g., cataracts).

Current strategies employed for corneal grafting make use of allogenic or synthetic materials. These strategies are only partially effective, however, and may stimulate host immune responses that result in tissue rejection. In addition, there is the potential for transfer of diseases from unhealthy donor organs. These issues are compounded by the growing use of corrective eye surgery which renders corneas unsuitable for grafting which will further impact the availability of acceptable allogenic supplies.

The use of grooved substrates has been demonstrated in the literature to induce cell and extracellular matrix (ECM) alignment upon various substrates (Ingber, 2003; Dalby et al., 2003; Walboomers et al., 1999; den Braber et al., 1998; Dunn and Brown, 1986). These methods have been employed in part as an effort to control tissue development. Most of the material substrates (i.e. titanium, silicone, PDMS and PEO) used in these studies are not readily degraded by the body or are not suitable for use in vivo. Hence, while possible applications in tissue development have been explored with these substrates, the cultured cells grown upon the substrates cannot be implanted, significantly limiting their practical use. Furthermore, these materials may cause stress induced cell responses that may disrupt normal cell function and tissue development over time.

Thus, what is needed in the art is a tissue-engineered cornea replacement system, made with a material that is optically clear, non-immunogenic, and biocompatible material. This invention answers that need.

SUMMARY OF THE INVENTION

This invention relates to a lamellae tissue layer, comprising a grooved silk fibroin substrate comprising tissue-specific cells. A multitude of lamellae tissue layers can be used to create a tissue-engineered organ having the lamellae tissue layers.

The invention also relates to a process for preparing a tissue-engineered organ. The process involves preparing a multitude of lamellae tissue layers. Each lamellae tissue layer comprises a grooved silk fibroin substrate seeded with tissue-specific cells capable of extracellular matrix deposition. The process then involves culturing the cells on the silk fibroin substrate for a sufficient period of time to allow for the cells and deposited extracellular matrix to form a tissue-engineered organ.

The invention also relates to a tissue-engineered cornea. The tissue-engineered cornea contains at least two lamellae tissue layers, an endothelial cell sheet on the bottom of the lamellae tissue layers, and an epithelial cell sheet on the top of the lamellae tissue layers. Each of the lamellae tissue layers comprise a grooved silk fibroin substrate seeded with fibroblast cells having an extracellular matrix deposition.

The invention also relates to an in vivo implantation system for tissue-engineered organs. The system involves forming a tissue-engineered organ comprising cultured tissue-specific cells on a grooved silk fibroin substrate; allowing the silk fibroin material in the tissue-engineered organ to at least partially degrade; and implanting the tissue-engineered organ into a native tissue.

The invention also relates to a kit for preparing a tissue-engineered organ. The kit includes a grooved silk fibroin substrate capable of receiving tissue-specific cells having an extracellular matrix deposition. The kit also includes instructions for seeding the tissue-specific cells on the silk fibroin substrate, organizing the silk fibroin substrates to form lamellae tissue layers, culturing the tissue-specific cells on the silk fibroin substrate, or a combination thereof.

The invention also relates to an in vitro testing system for animal organ replacement. The system involves forming a cultured tissue system comprising cultured tissue-specific cells on a grooved silk fibroin substrate; incubating the cultured tissue system for a time period until the tissue construct of the tissue-specific cells is able to maintain native tissue characteristics and form cultured tissue; and testing the cultured tissue under in vitro research conditions to aid in the development of animal organ replacement.

The wide range of potential use, mechanical robustness, incorporated vasculature, and all-natural material composition of the silk tissue construct offers a significant advancement in tissue engineering technology. Using silk as a substrate brings together both the ability to better control cell and ECM development, while also offering the advantage of substrate material removal over time.

BRIEF DESCRIPTION OF THE FIGURES

FIG. 1 depicts silk films with cast microgrooves. FIG. 1(a) is a field-emission scanning electron microscope (FE-SEM) image of groove topology. FIG. 1(b) is an atomic force microscope (AFM) of film surface. In these figures, each groove is approximately 1.7 μm in width and 1 μm in depth.

FIG. 2 depicts aligned corneal fibroblasts cells cultured upon grooved silk lamellae substrates. FIGS. 2(a) and (c) show the transmission (a) and false color confocal images (d) of green fluorescent protein (GFP) labeled corneal fibroblasts growing on non-patterned silk films. FIGS. 2(b) and (d) show the transmission (b) and false color confocal images (d) of GFP labeled corneal fibroblasts growing on a groove-patterned silk lamellae surface. Scale bar is 100 um.

FIG. 3 depicts scanning electron microscope (SEM) images of aligned fibroblasts corneal cells and ECM on grooved silk lamellae constructs. FIGS. 3(a) and (c) show fibroblasts and ECM aligning on grooved silk lamellae. FIG. 3(b) depicts a magnified image of an aligned cell process and clear image of patterned groove geometry upon the silk lamellae.

FIG. 4 depicts corneal fibroblasts aligned on silk films and cast with circular geometrical patterns. FIG. 4(a) shows a fluorescent image of GFP labeled corneal fibroblasts grown on circular patterned silk films, and FIG. 4(b) shows a digitally enhanced higher magnification image of the same. FIG. 4(c) shows a circular-patterned cast that can be used for silk films.

FIG. 5 depicts SEM images of laser ablated micropores in silk lamellae construct. FIG. 5(a) is a line of micropores about 5 microns in diameter. Scale bar is 50 urn. FIG. 5(b) is a high-magnification image of a select micropore, which is also about 5 µm in diameter.

FIG. 6 shows graphs of Alamar Blue metabolic assays for rabbit corneal fibroblast cultures grown on different substrates for 10 days. FIG. 6(a) shows a graph of the cultures at day 1; FIG. 6(b) shows the cultures at day 4; and FIG. 6(c) shows the cultures at day 10.

FIG. 7 depicts phase contrast images of corneal fibroblasts after 14 days in culture on (a) silk coated glass and (b) tri-calcium phosphate (TCP) coated glass. The images are magnified by 320×. Immunofluorescent images for corneal fibroblasts after four days in culture on (c) silk-coated glass and (d) glass. The lighter areas, shown as green fluorescence in the color images, demonstrate collagen V protein expression.

FIG. 10 depicts images of aligned corneal fibroblasts. FIG. 10(a) shows the corneal fibroblasts within the central region of the silk cornea construct. Multiple layers of cells can be seen below focus plane of cells. FIG. 10(b) shows the corneal fibroblasts growing on grooved-silk lamellae constructs.

FIG. 11 depicts SEM images of silk films (a) produced with poly(ethylene) oxide (PEO) phase separation and exhibiting porosity (b) silk films produced without PEO phase separation.

DETAILED DESCRIPTION

Figure 8:
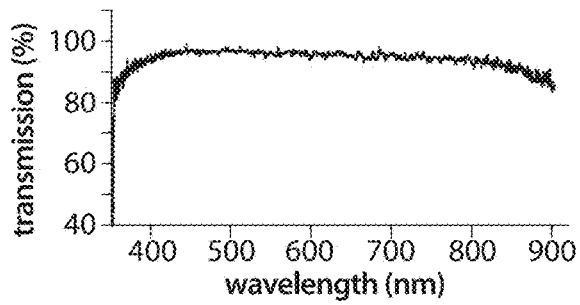
FIG. 8 is a graph showing the percentage of light that is transmitted through a 30-micron silk fibroin film.

This invention relates to a lamellae tissue layer, comprising a grooved silk fibroin substrate comprising tissue-specific cells. A multitude of lamellae tissue layers can be used to create a tissue-engineered organ having the lamellae tissue layers.

Silk fibroin provides a versatile material for constructing lamellae tissue layers. The stability (good strength and toughness), biocompatibility (less immunogenic and pro-inflammatory than collagens or polyesters), slow degradability, purity (no known bioburdens), and modifiability (easily modified to achieve specific cell-binding or cell-activation characteristics) make silk fibroin an ideal candidate for preparing lamellae tissue layers and tissue-engineered organs. Tissue-engineered corneas are particularly desirable because of the transparency of the silk fibroin, including its ability to transmit nearly 100% of visible light.

The tissue-specific cells may be any biological cells of the desired tissue. For instance, if the desired tissue is a cornea, then the tissue-specific cells should be biological cells having corneal properties or being capable of being used with other biological cells having corneal properties. Suitable tissue-specific cells include, but are not limited to, stem cells, fibroblasts, endothelial, epithelial, adipose cells capable of generating tissue-specific extracellular matrix, and combinations thereof.

The grooved silk fibroin substrate is a fabricated silk film designed to induce cell and extracellular matrix alignment. Preferably, the thickness of grooved silk fibroin substrate ranges from about 10 nm to about 1 mm, the groove size is at least 125 nm, and the groove thickness depth is at least 100 nm. More preferably, the thickness of grooved silk fibroin substrate ranges from about 100 nm to about 100 µm, the groove size ranges from about 500 nm to about 10 µm, and the groove thickness depth ranges from about 250 nm to about 5 µm. Most preferably, the thickness of grooved silk fibroin substrate ranges from about 500 nm to about 10 µm, the groove size ranges from about 1 µm to about 5 µm, and the groove thickness depth ranges from about 500 nm to about 3 µm. [confirm preferred ranges] The silk diffraction gratings may be characterized for surface morphology by known techniques, such as field emission scanning electron and atomic force microscopy. See FIG. 1.

Any type of silk fibroin may be used to make the silk fibroin substrate. Silk fibroin produced by silkworms is the most common and is generally preferred. However, there are many different silks, including spider silk, transgenic silks, genetically engineered silks, and variants thereof, that may alternatively be used. As used herein, the term "fibroin" includes silkworm fibroin and insect or spider silk protein (Lucas et al., Adv. Protein Chem 13: 107-242 (1958)). Preferably, fibroin is obtained from a solution containing a dissolved silkworm silk or spider silk. The silkworm silk protein may be obtained, for example, from *Bombyx mori*, and the spider silk is obtained from *Nephila clavzes*. In the alternative, the silk proteins can be obtained from a solution containing a genetically engineered silk, such as from bacteria, yeast, mammalian cells, transgenic animals or transgenic plants. See, for example, PCT Publication WO 97/08315 and U.S. Pat. No. 5,245,012, both of which are herein incorporated by reference in their entirety.

An aqueous silk fibroin solution may be prepared from the silk fibroin using techniques known in the art. Suitable processes for preparing silk fibroin solution are disclosed in PCT Application No. PCT/US2004/011199, and U.S. Provisional Application No. 60/856,297, filed Nov. 3, 2006, entitled "Biopolymer Photonic Crystals and Method of Manufacturing the Same," both of which are herein incorporated by reference in their entirety.

For instance, the silk fibroin solution may be obtained by extracting sericin from the cocoons of a silkworm silk, such as *Bombyx mori*. For example, *B. mori* cocoons can be boiled for about 30 minutes in an aqueous solution, preferably an aqueous solution having about 0.02M $Na_2CO_3$. The cocoons can then be rinsed with water, for example, to extract the sericin proteins. The extracted silk can then be dissolved in an aqueous solution, preferably an aqueous salt solution. Salts useful for this purpose include lithium bromide, lithium thiocyanate, calcium nitrate or other chemicals capable of solubilizing silk. Preferably, the extracted silk is dissolved in about 9-12 M LiBr solution. The salt may later be removed using, for example, dialysis.

Alternatively, the silk fibroin solution may be obtained from a solution containing a dissolved spider silk, such as *Nephila ciavipes*. The silk fibroin solution can also be obtained from a solution containing a genetically engineered silk. The genetically engineered silk can, for example, comprise a therapeutic agent, e.g., a fusion protein with a cytokine, an enzyme, or any number of hormones or peptide-based drugs, antimicrobials and related substrates.

Biocompatible polymers can also be added to the silk solution to generate composite matrices. Biocompatible polymers useful in the compositions described herein include, for example, polyethylene oxide (PEO) (U.S. Pat. No. 6,302,848), polyethylene glycol (PEG) (U.S. Pat. No. 6,395,734), collagen (U.S. Pat. No. 6,127,143), fibronectin (U.S. Pat. No. 5,263,992), keratin (U.S. Pat. No. 6,379,690), polyaspartic acid (U.S. Pat. No. 5,015,476), polylysine (U.S. Pat. No. 4,806,355), alginate (U.S. Pat. No. 6,372,244), chitosan (U.S. Pat. No. 6,310,188), chitin (U.S. Pat. No. 5,093,489), hyaluronic acid (U.S. Pat. No. 387,413), pectin (U.S. Pat. No. 6,325,810), polycaprolactone (U.S. Pat. No. 6,337,198), polylactic acid (U.S. Pat. No. 6,267,776), polyglycolic acid (U.S. Pat. No. 5,576,881), polyhydroxyalkanoates (U.S. Pat. No. 6,245,537), dextrans (U.S. Pat. No. 5,902,800), and polyanhydrides (U.S. Pat. No. 5,270,419). Two or more biocompatible polymers can be used in combination.

The silk fibroin substrate may be prepared by casting a silk solution onto patterned diffractive optical surfaces, such as different holographic diffraction gratings with varying line pitches as masks. After the silk solution has been cast, they can be dried as films. Drying may be accomplished by any means known in the art. For instance, the films may be placed in a vacuum environment and water annealed for two or more hours, removed, and allowed to further dry. Removal from the grating mask can be accomplished by simple mechanical lifting of the grating from the substrate.

The grooves of the silk fibroin substrate induce cell and ECM alignment. Thus, the tissue-specific cells have deposited extracellular matrix on the substrate. See FIG. 2. The cultured cells grown on the silk films align and form their ECM parallel to the grooved film pattern. See FIGS. 2 and 3. This allows one to control the direction of cell orientation and tissue alignment upon the lamellae layer, something that is helpful in tissue formation. Geometrical shapes imprinted on the substrates may also be used to grow the cells in aligned patterns. See FIG. 4. Varying the geometrical pattern upon the silk film allows for defined spatial patterning of cell growth for the targeted tissue system.

The individual lamellae tissue layers, each of which is virtually a two-dimensional (2-D) construct containing the silk film and tissue-specific cell types, can then be stacked upon one another or otherwise combined to produce a three-dimensional (3-D) tissue-engineered organ. These 2-D lamellae structures can thus serve as "building-blocks" for 3-D tissue engineered constructs. Such a system exploits the advantageous material features of silk fibroin, including its slow degradation, biocompatibility, optical transparency, and durability for handling and suturing.

The edges of the multi-layer construct may be sealed to prevent diffusion. Because the silk substrates are self adhering when exposed to applied pressure, a dulled biopsy punch which corresponds to the round silk film geometry can be used to apply pressure upon seeding. Alternatively, polydimethylsulfoxide (PDMS) discs of similar diameter to the silk substrate may be employed to act as a clamping mechanism to hold the layers in place. PDMS has been shown to be inert in cell culture, has low water sorption, and can induce a passive clamping force. If the self-adherence mechanism is not sufficient, fibrin glue or similar adhesive can also be used.

In view of the inherent control and ability of the protein found in the silk fibroin, the functional material requirements of the desired tissue system can be closely matched and then interfaced with the tissue specific cell type. The lamellae "building-block" tissue system is applicable to multiple organ systems, provides a range of tunable material properties, and is completely, or at least mostly, composed of biomaterials that are non-immunogenic upon implantation. The resulting tissue-engineered organ thus contains silk fibroin substrates with cultured cells and deposited extracellular matrix.

Because of diffusion limitations, cells located in the central regions of tissue-engineered organs many times do not receive sufficient levels of nutrients required to support cellular life. To better support cell viability, the tissue-engineered organs may contain a vasculature network able to supply nutrient diffusion throughout the entire tissue-engineered construct. Incorporating micropores into the tissue-engineered organ mimics the convection for efficient nutrient transport and allows for nutrient diffusion or vascularization to each lamellae tissue layer of the biological construct.

The vasculature-like micropores may be "drilled" in defined patterns within the silk film using polymer phase separation chemistry, laser ablation techniques, or other techniques known in the art. Laser ablation technology, such as Femtosecond laser ablation technology, involves high energy pulsed laser light to minimize peripheral damage to the material. Polymer phase separation chemistry involves mixing two polymers that do not mix well (immiscible, akin to oil and water) to exploit their inability to mix well, such that they separate into different domains to generate materials morphologies based on the polymers and their respective amounts. Preferred polymers for use in polymer phase separation include polyethylene oxide or similar alternative polymers and waxes.

Porosity within the silk films can often times be systematically controlled. When using laser ablation technology, porosity can be altered based on the size or the focus of the laser. When using polymer phase separation chemistry, porosity size range and pore density can be controlled by varying the concentration of the polymer. By holding constant the other variables, such as casting volume, casting surface area and silk concentration (or multiple variables changed at the same time), porosity can be dependent, do a large degree, on polymer concentration. See Example 4.

The micropores should be small enough so that the material properties of the lamellae tissue layers are not compromised and can still maintain a robust matrix for tissue development, yet large enough to provide the desired vascularization. Preferably, the average diameter of the micropores ranges from about 100 nm to about 100 micron. More preferably, the average diameter ranges from about 800 nm to about 20 micron. Most preferably, the average diameter ranges from about 1 micron to about 10 micron. [confirm preferred ranges]. See FIG. 5.

The micropores are preferably incorporated into the tissue-engineered organ in patterns designed to optimize nutrient diffusion to culture surface area specific to the targeted tissue system. As the layers are stacked upon one another, the microporous structure allows for nutrient diffusion to all regions of the 3-D construct.

Various designs or patterns can be used when creating the micropores. For tissue-engineered corneas, a 50-100 µm spacing is preferred because it provides an averaged spaced vascular network similar to that found in corneal tissue (although corneal tissue is not vascularized by blood capillaries, it contains a network that assists in nutrient diffusion through the tissue). Generating arrays of micron- or nano-sized holes interspersed in grid spacing provides nutrient diffusive ports throughout the stacked silk lamellae tissue layers.

The lamellae tissue layers may be used to produce various tissue types and organ systems. Such systems may include bone, skin, cardiac tissue, cardiac muscle, muscle tissue, dense connecting tissue, basement membranes, smooth muscle tissue, endothelial tissue, and nervous tissue. The organ can be made up of any tissue that can be formed by the assembly of the silk fibroin substrates with cultured cells and deposited extra cellular matrix. Preferably, the organ is a cornea, which is particularly suited for silk-based lamellae tissue layers because of the optically clear, non-immunogenic properties, and biocompatibility of the silk fibroin.

The invention also relates to a process for preparing a tissue-engineered organ. The process involves preparing a multitude of lamellae tissue layers. Each lamellae tissue layer comprises a grooved silk fibroin substrate seeded with tissue-specific cells capable of extracellular matrix deposition. The process then involves culturing the cells on the silk fibroin substrate for a sufficient period of time to allow for the cells and deposited extracellular matrix to form a tissue-engineered organ. Optionally, the process also involves creating micropores in the silk film. Through the use of silk fibroin, the tissue-engineered organ can be both non-immunogenic and biocompatible.

Seeding the silk fibroin substrate may be accomplished through means known in the art. Generally, the cells should be seeded in the substrate in a manner that best enables their ability to be cultured within the substrate construct. For example, the cells should typically be distributed at a density of about 1000 cells/cm$^2$ to about 50,000 cells/cm$^2$. Preferably, the cells should be distributed at a density of about 5000 cells/cm$^2$ to about 20,000 cells/cm$^2$. Of course, these distribution patterns may differ depending on the size of the cell, the seeding conditions, and other factors appreciated by those of skill in the art.

When seeding the cells in the silk substrate, the cells may be supplemented with other materials known in the art to promote cell growth. Materials known to promote cell growth include cell growth media, such as Dulbecco's Modified Eagle Medium (DMEM), fetal bovine serum (FBS), non-essential amino acids and antibiotics, and growth and morphogen factors such as basic fibroblast growth factor (bFGF), transforming growth factors (TGFs), Vascular endothelial growth factor (VEGF), insulin-like growth factor (IGF-I), bone morphogenetic growth factors (BMPs), nerve growth factors and related proteins.

Additional materials that can be included when seeding the cell include DNA, siRNA, antisense, plasmids, liposomes and related systems for delivery of genetic materials; peptides and proteins to active cellular signaling cascades; peptides and proteins to promote mineralization or related events from cells; adhesion peptides and proteins to improve gel-tissue interfaces; antimicrobial and antifungal peptides and proteins and related compounds. The additional materials can also include common components found in pharmaceutical formulations, such as known excipients. Exemplary excipients include diluents, solvents, buffers, solubilizers, suspending agents, viscosity controlling agents, binders, lubricants, surfactants, preservatives and stabilizers.

The silk fibroin substrate of the lamellae tissue layers provides a mechanically robust matrix to support cellular growth until the culture has reproduced at least part of its original matrix. The amount of time involved in culturing the cells is dependent on the type of cells used, the conditions of the culturing, the degree to which the culture should represent the original matrix, and other variables appreciated by those of skill in the art. Typically, after the silk fibroin substrate has been seeded, the cells are cultured for approximately 1-6 weeks, whereupon the silk fibroin protein will have been at least partially degraded and the new tissue construct exhibits properties consistent with those of the original matrix. It is at this point that the tissue-engineered organ is typically ready for in vivo use or as a tissue system for ex vivo studies.

The cells may be cultured in accordance with techniques known in the art. For instance, the cells may be cultured in an organotypic environment, such as in submerged culture, at air-liquid interfaces or in selective perfusion bioreactors, or other environments suitable for culture cells on silk fibroin substrates.

When preparing a tissue-engineered cornea, an endothelial cell sheet may be added on the bottom of the lamellae tissue layers and an epithelial cell sheet may be added on the top of the lamellae tissue layers. In this preferred embodiment, the invention relates to a tissue-engineered cornea containing at least two lamellae tissue layers, an endothelial cell sheet on the bottom of the lamellae tissue layers, and an epithelial cell sheet on the top of the lamellae tissue layers. Each of the lamellae tissue layers comprise a grooved silk fibroin substrate seeded with fibroblast cells having an extracellular matrix deposition. Preferably, the cornea is optically clear, non-immunogenic, and biocompatible, and the lamellae tissue layers comprise micropores that allow for nutrient diffusion to each layer.

The invention also relates to an in vivo implantation system for tissue-engineered organs. The system involves forming a tissue-engineered organ comprising cultured tissue-specific cells on a grooved silk fibroin substrate; allowing the silk fibroin material in the tissue-engineered organ to at least partially degrade; and implanting the tissue-engineered organ into a native tissue. The in vivo implantation system may be applicable to multiple organ systems, provides a range of tunable material properties, and is completely, or at least mostly, composed of biomaterials that are non-immunogenic upon implantation.

The determination of when a tissue-engineered organ is ready for implantation should generally be left to the expertise of the skilled artisan. Typically, implantation into a native tissue may be done when the silk fibroin material has at least partially degraded and the culture has reproduced to a point at or near its original matrix.

The invention also relates to a kit for preparing a tissue-engineered organ. The kit includes a grooved silk fibroin substrate capable of receiving tissue-specific cells having an extracellular matrix deposition. The kit also includes instructions for seeding the tissue-specific cells on the silk fibroin substrate, organizing the silk fibroin substrates to form lamellae tissue layers, culturing the tissue-specific cells on the silk fibroin substrate, or a combination thereof. The instructions need only be provided in detail sufficient to enable a skilled artisan to use the kit consistent with its primary use of preparing a tissue-engineered organ.

The kit may additionally include other tools known in the art to be helpful in preparing a tissue-engineered organ. For example, the kit may contain a collecting and containment tool set for acquiring cells from a primary cell source, such as a human or an animal. The kit may also contain a bioreactor for culturing the silk fibroin substrate after the substrate has been seeded with the tissue-specific cells. The bioreactor is preferably capable of maintaining sterile and nutrient-filled conditions until the tissue-specific cells have been cultured.

Various uses of the kit are contemplated. The kit may be used in the academia and industry for commercial testing or other types of commercial use. In a preferred embodiment, the kit may be used to prepare a tissue-engineered organ for commercial testing purposes.

The invention also relates to an in vitro testing system for animal organ replacement. The system involves forming a cultured tissue system comprising cultured tissue-specific cells on a grooved silk fibroin substrate; incubating the cultured tissue system for a time period until the tissue construct of the tissue-specific cells is able to maintain native tissue characteristics and form cultured tissue; and testing the cultured tissue under in vitro research conditions to aid in the development of animal organ replacement.

The time period for incubating the cultured tissue system varies depending on the tissue system, the incubation conditions, the amount of organ that is being replaced, and other variables appreciated by those of skill in the art. If only a small portion of an organ is being replaced under favorable incubation conditions, the time period will obviously be shorter than if a large portion or a complete organ is being replaced under strained conditions. The exact time period can be determined by one of skill in the art under the circumstances of the organ replacement. Typically, the cultured tissue system is incubated for approximately 1-6 weeks.

Testing the cultured tissue involves any aspects of testing that one of skill in the art would typically conduct in a research setting. The results, or lack of results, obtained through this testing should be viewed as aiding in the development of animal organ replacement.

Unless otherwise defined, all technical and scientific terms used herein have the same meaning as commonly understood by one of ordinary skill in the art. Although methods and materials similar or equivalent to those described herein can be used in the practice or testing of the invention, the preferred methods and materials are described below. All publications, patent applications, patents and other references mentioned herein are incorporated by reference. In addition, the materials, methods and examples are illustrative only and not intended to be limiting. In case of conflict, the present specification, including definitions, controls.

The invention will be further characterized by the following examples which are intended to be exemplary of the invention.

EXAMPLES

Example 1

Silk as a Substrate for Corneal Cell Growth

Silk has been shown to be a viable substrate for a number of different cell types. Silk tissue layers are also capable of supporting corneal cell growth comparative to tissue culture plastic using the Alamar Blue metabolic cell assay. See FIG. 6. As shown in FIG. 6, similar cellular metabolic rates were found upon silk, glass and TCP substrates. These data show the ability to produce lamellae tissue layers as building-blocks for tissue-engineering purposes. It also provides support for the production of silk tissue-engineered cornea.

Example 2

Rabbit Stromal Fibroblasts

The ability of rabbit stromal fibroblasts to grow on silk fibroin substrates was assessed. A monolayer of 8% fibroin solution was deposited on 12 mm round glass coverslips using a spin coater (Laurel! Technologies). The spin coater produces an even distribution of the fibroin polymer across the glass surface. The fibroin coated coverslips were steam sterilized and placed within 24-well culture dishes. Primary corneal fibroblasts were isolated from adult rabbit corneas and cultured to confluency on TCP. The cells were then seeded at a density of 10,000 cells/cm$^2$ on the fibroin coated coverslips, and supplemented with media containing Dulbecco's Modified Eagle Medium (DMEM), 10% fetal bovine serum (FBS), and 1% Penstrep (an antibiotic treatment to reduce contamination of the cell cultures). The cells where grown to confluency and the morphology of the cells appeared similar to fibroblasts grown on TCP. See FIG. 7.

To ensure that the cultured cells were stromal fibroblasts, immunostaining was used to localize collagen V, a protein produced in abundance by corneal stromal fibroblasts. Collagen V is produced by corneal keratocytes in situ within the stromal matrix and acts to regulate collagen fibril diameter. See Marchant et al., 1996; and Birk et al., 1990, both of which are herein incorporated by reference in their entirety. The immunostaining provides evidence that this protein was generated by the corneal fibroblasts seeded on the silk fibroin substrates. These preliminary results suggest that rabbit corneal fibroblasts retain their differentiated phenotype on silk fibroin substrates.

Example 3

Tissue-Engineered Silk Cornea

Silk fibroin substrates may be transformed into lamellae tissue layers capable of guiding cell and ECM development and can also be vascularized or porous networks generated to support nutrient diffusion. These lamellae tissue layers can then be combined to form a 3-D tissue construct, or a tissue-engineered organ.

The corneal tissue system offers a unique set of parameters that make it a useful model system for the use of the lamellae structures, in that the tissue is largely composed of stacked layers of extracellular matrix interspersed with cell layers. The lamellae tissue layers provide the correct set of material characteristics needed to form corneal tissue in that silk fibroin is robust in its mechanical properties, degrades naturally with native tissue replacement by the seeded cells, is non-immunogenic, and is optically clear with near 100% transmission of visible light. See FIG. 8.

Figure 9:
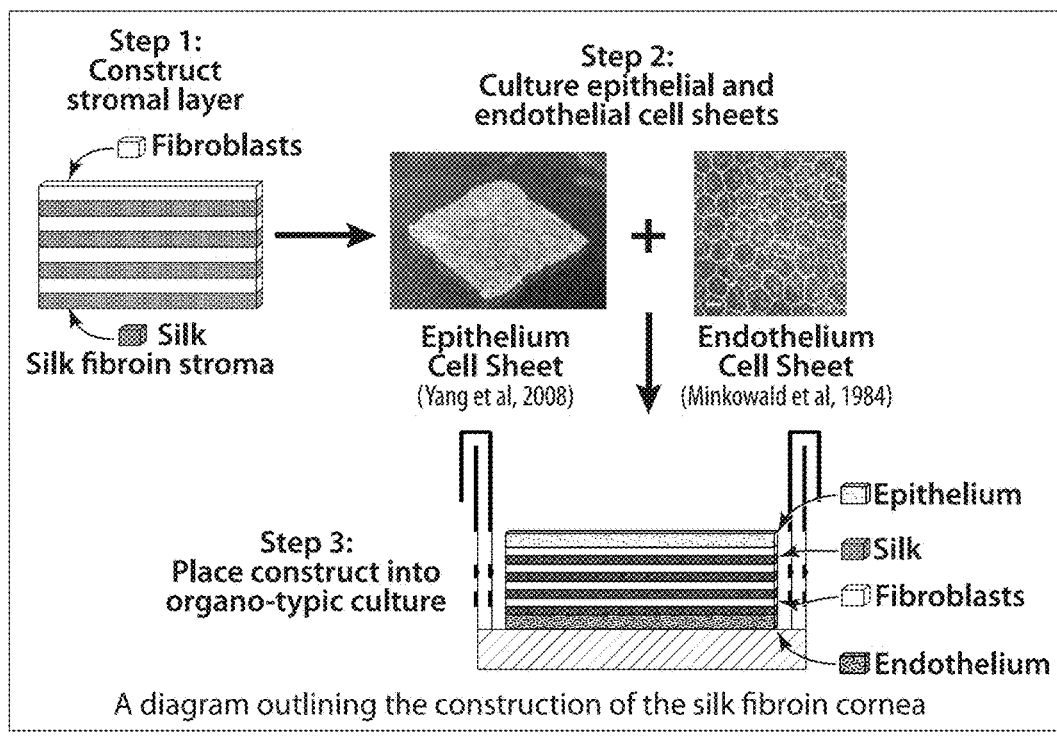
FIG. 9 depicts a schematic of a preferred method of constructing a silk-engineered cornea.

The tissue layers may be used to produce tissue-engineered organs, such as corneal stromal tissue analogs. A schematic of a process that can be used to form an entire corneal tissue is shown FIG. 9. Other configurations can also be used. In FIG. 9, stacked lamellae tissue layers are placed between endothelial and epithelial cell sheets on the bottom and top of the stacked stroma region respectively. See Nishida et al., 2003, herein incorporated by reference in its entirety, for a description of the endothelial and epithelial cell sheets.

The entire tissue-engineered organ can then be cultured in an organotypic environment until it is ready for implantation or ex vivo tissue experimentation. Studies show that cell growth was detected within the central regions of the tissue-engineered silk cornea construct, suggesting cell viability is present throughout the construct. See FIG. 10.

Example 4

Controlling Silk Film Porosity by PEO Phase Separation

Materials: 8% silk solution, 5% poly(ethylene oxide) (PEO) solution, water and methanol were used. A desiccator, polydimethysulfoxide (PDMS) substrates, Teflon cover slips, a Teflon drying surface, tube racks, tweezers, 1-mL, syringes, micro-centrifuge tubes, and 24-well plates.

Methods: A silk fibroin aqueous solution is prepared using standard protocols known in the art. The silk/PEO films are cast on PDMS, such as patterned or flat surfaces. A 5% wt. vol. PEO solution was prepared. 100-uL of silk/PEO solution dilution was cast onto 2-$cm^2$ patterned and flat round PDMS surfaces. The film was allowed to dry for 12-hrs. Upon drying, the films were water annealed for 6-hrs to induce primary beta-sheet crystallinity. After water annealing, the films were submerge in a water bath to prevent excessive film dehydration. The water bath was covered and the films allowed to sit for 24-hrs. One film was transferred from the water bath into a 100% MeOH bath for secondary beta-sheet crystallinity induction. The film was allowed to sit for 2-minutes, and then peeled off of their respective PDMS surfaces while submerged in the methanol bath. Once removed, the films were floated onto a Teflon coated glass slide, removed from the MeOH bath, and placed onto a Teflon coated drying surface (i.e. acrylic coated surfaces).

Results: Micro-pores were created within silk films by using PEO phase separation chemistry techniques to promote increased nutrient diffusion and cell-to-cell interaction throughout a stacked film construct. See Jin et al., 2004, herein incorporated by reference in its entirety. The ratio of silk-to-PEO used in casting directly influenced the pores generated in the films once formed, dried and the PEO is extracted. Pores ranging between 1-3 microns in diameter were produced within the film. See FIG. 11(a). In contrast, no pores were exhibited in controls not using the PEO separation method. See FIG. 11(b) as a comparative example.

REFERENCES

Abraham, M., Hassanisadi, M., Jalali-Heravi, M., Ghafourian, T., Cain, W., and Cometto-Muniz, J. (2003). "Draize rabbit eye test compatibility with eye irritation thresholds in humans: a quantitative structure-activity relationship analysis" *Toxicological Sciences*, 76:384-391.

Alaminos, M., Del Carmen Sanchez-Quevedo, M., Munoz-Avila, J. I., Serrano, D., MediaIdea, S., Carreras, I., Campos, A. (2006). "Construction of a complete rabbit cornea substitute using a fibrin-agarose scaffold." *Invest Opthamol Vis Sci*, 47(8):331 1-3317.

Altman, G., Diaz, F., Jakuba, C., Calabro, T., Horan, R., Chen, J., Lu, H., Richmond, J., and Kaplan, D. (2003). "Silk-based biomaterials." *Biomaterials*, 24:401-416.

Altman, G., Horan, R., Lu, H., Moreau, J., Martin, I., Richmond, J., and Kaplan, D. (2002a). "Silk matrix for tissue engineered anterior cruciate ligaments." *Biomaterials*, 23:4131-4141.

Altman, G., Horan, R. Martin, I., Farhadi, J., Stark, P., Volloch, V., Vunjak-Novakovic, C., Richmond, J., and Kaplan, D. (2002b). "Cell differentiation by mechanical stress." *The FASEB Journal*, 16:270-272.

Auger, F., Remy-Zolghadri, M., and Grenier, G. (2002). "A truly new approach for tissue engineering: the LOEX self-assembly technique." *Ernst Schering Res Found Workshop*, 35:73-88.

Berryhill, B. L., Kane, B., Stramer, B. M., Fini, M E., Hassell, J R. (2003). "Increased SPARC accumulation during conical repair." *Exp Eye Res.*, 77(1):85-92.

Bettinger, C., C. Cyr, J. Borenstein, R. Langer, D. L. Kaplan (2007). Microfluidic devices from silk fibroin. *Adv. Materials, in press*.

Birk, D., Fitch, J., Babiarz, J., Doane, K., and Linsenmayer, T. (1990). "Collagen fibrillogenesis in vitro: interaction of types I and V collagen regulates fibril diameter." *J Cell Science*, 95(4):649-657.

Birk, D., Fitch, J., Babiarz, J., and Linsenmayer, T. (1988). "Collagen type I and V are present in the same fibril in the avian corneal stroma." *J Cell Biol*, 106:999-1008.

Boisjoly, H., Tourigny, R., Bazin, R., Laughrea, P., Dube, I., Chamberland, G., Bernier, J., and Roy, R. (1993). "Risk factors of corneal graft failure." Ophthalmology, 100 (11):1 728 1 735.

Bradley, 3., Kelley, M., Zhu, X., Anderssohn, A., Alexander, J., and Acott, T. (2001). "Effects of mechanical stretching on trabecular matrix metalloproteinases." *Invest Ophthalmol Vis Sci*, 42:1505-1513.

Breen, E. (2000). "Mechanical strain increases type 1 collagen expression in pulmonary fibroblasts in vitro." *J Applied Physiology*, 88:203-209.

Bryant, M., Szerenyi, K., Schmotzer, H., and McDonnell, P. (1994). "Corneal tensile strength in fully healed radial keratotomy wounds." *Invest Ophthalmol Vis Sci*, 35(7): 3022-3031.

Carlsson, D., Li, F., Shimniura, S., and Griffith, M. (2003). "Bioengineered corneas: how close are we?" *Current Opinions in Ophthalmology*, 14:192-197.

Chaloin-Dufau, C., Sun, T., and Dhouailly, D. (1990). "Appearance of the keratin pair K3/K12 during embryonic and adult corneal epithelial differentiation in the chick and in the rabbit." *Cell Differ Dev*, 32:97-108.

Chiquet, M., Matthisson, M., Koch, M., Tannheimer, M., and Chiquet-Ehrismann, R. (1996). "Regulation of extracellular matrix synthesis by mechanical stress." *Biochem Cell Biol*, 74:737-744.

Cintron, C., Covington, H., and Kublin, C. (1983). "Morphogenesis of Rabbit Conical Stroma." *Invest Opthalmol*, 24:543-556.

Conn, A., Durrant, L., and Spendlove, I. (1999). "Delivery of pCMV-S DNA using the Helios gene gun system is superior to intramuscular injection in Balb/c Mice." *Gene Transfer*, Bio-Rad Laboratories, Inc. Bulletin, 2726:1-4.

Cunniff, P., Fossey, S., Auerbach, M., Song, J., Kaplan, D., Adams, W., Eby, R., Mahoney, D., and Vezie, D. (1994). "Mechanical and thermal properties of dragline silk from the spider *Nephila clavipes.*" *Poly. Adv. Technol.*, 5:401-410.

Dalby, M. J., Riehle, M O., Yarwood, S. J., Wilkinson & Curtis A. S. G. (2003). "Nucleus alignment and cell signaling in fibroblasts: response to a micro-grooved topography." *Exp. Cell Res* 284, 274-282.

den Berg, T. V. and Tan, K. (1994). "Light transmittance of the human cornea from 320 to 700 nm" *Vision Research*, 34:1453-1456.

den Braber, E. T., de Ruijter, J. E., Ginsel, L. A., von Recum, A. F. & Jansen, J. A. (1998). "Orientation of ECM protein deposition, fibroblast cytoskeleton, and attachment complex components on silicone microgrooved surfaces." *J Biomed Mater Res* 40, 291-300.

Doane, K., Babiarz, J., Fitch, J., Linsenmayer, T., and Birk, D. (1992). "Collagen fibril assembly by corneal fibroblasts in three-dimensional collagen gel cultures: small diameter heterotypic fibrils are deposited in the absence of keratan sulfate proteoglycan." *Exp Cell Res*, 202:1 13-124.

Donohue, D., Stoyanov, B., McCally, R., and Farrell, R. (1995). "Numerical modeling of the cornea's lamellar structure and birefringence properties." *J Optical Society of America A*, 12 (7):1425-1438.

Dunn, G A. & Brown, F. (1986). "Alignment of fibroblasts on grooved surfaces described by a simple geometric transformation." *J Cell Sci*, 83:313-340.

Eastwood, M., Mudera, V., McGrouther, D., and Brown, R. (1998). "Effect of precise mechanical loading of fibroblast populated collagen lattices: morphological changes." *Cell Motility and the Cytoskeleton*, 40:13-21.

Ethier, C., Johnson, M., and Ruberti, J. (2004). "Ocular Biomechanics and Biotransport." *Annual Review of Biomedical Engineering*, 6:249-273.

Franks, T. (2003). "EU bans animal testing for cosmetics." *BBC News*, 1:1.

Garate, M., Marchant, J., Cubillos, I., Cao, Z., Khan, N., and Panjwani, N. (2006). "In vitro pathogenicity of *Acanthamoeba* is associated with the expression of the mannose-binding protein." *IOVS*, 47:1056-1062.

Gaudreault, M., Carrier, P., and Larouche, K. (2003). "Influence of Sp1/Sp3 expression on corneal epithelial cells proliferation and differentiation properties in reconstructed tissues." *Invest Ophthalmol Vis Sci*, 44:1447-1457.

Gipson, I., Spurr-Michaud, S., and Tisdale, A. (1988). "Hemidesmosomes and anchoring fibril collagen appear synchronously during development and wound healing." *Develop Biol*, 126(2):253-262.

Gordon, M., Foley, J., Lisenrnayer, T., and Fitch, J. (1996). "Temporal expression of types XII and XIV collagen mRNA and protein during avian corneal development." *Dev Dyn*, 206:49-58.

Gosline, J., DeMont, M., and Denny, M. (1986). "The structure and properties of spider silk." *Endeavour*, 10:37-43.

Hofmann, S., Foo, C. W. P., Rossetti, F., Textor, M., Vunkak-Novakovic, G., Kaplan, D., Merkle, H., and Meinel, L. (2006). "Silk fibroin as an organic polymer for controlled drug delivery." *J Controlled Release*, 111:219-227.

Hogan, M., Alvarado, J., and Weddell, J. (1971). "Histology of the Human Eye." Saunders.

Horan, R., Antic, K., Collette, A., Wang, Y., Huang, J., Moreau, J., Volloch, V., Kaplan, D., and Altman, G. (2005). "In vitro degradation of silk fibroin." *Biomaterials*, 26:3385-3393.

Hu, X., Lui, W., Cui, L., Wang, M., and Cao, Y. (2005). "Tissue engineering of nearly transparent corneal stroma." *Tissue Engineering*, 11:1710-1717.

Ingber, D. E. (2003). "Tensegrity II. How structural networks influence cellular information processing networks." *J of Cell Sci*, 116:1397-1408.

Jacobs, J. and Taravella, M. (2005). "Corneal graft rejection." *eMedicine*, 1:1-3.

Jester, J. V., Barry, P. A., Lind, G. J., Petroll, W. M., Garana, R., Cavanagh, H. D. (1994). "Corneal keratocytes: in situ and in vitro organization of cytoskeletal contractile proteins." *Invest Opthalmol Vis Sci*, 35(2):730-743.

Jin, H. and Kaplan, D. (2003). "Mechanism of silk processing in insects and spiders." *Nature*, 424:1057-1061.

Jin. H., Park, J., Karageorgiou, V., Kim, U., Valluzzi, R., Cebe, P., and Kaplan, D. (2005). "Water-Stable Silk Films with Reduced-Sheet Content." *Adv Func Mats*, 15:1241-1247.

Joyce, N. C. (2003). "Proliferative capacity of the corneal endothelium." *Prog Retin Eye Res*, 22(3):359-389.

Jumblatt, M. and Neufeld, A. (1983). "Beta-adrenergic and serotonergic responsiveness of rabbit corneal epithelial cells in culture." *Invest Ophthalmol Vis Sci*, 24:1139-1143.

Kalayoglu, M. (2006). "In search of the artificial cornea: recent developments in keratoprostheses." *MedCompare, Opthalmology*:1.

Kaminski, S., Lukas, R., Koyuncu, D., and Grabner, G. (2002). "Corneal sensitivity 10 years after epikeratoplasty." *J Refract Surg*, 18:731-736.

Karageorgiou, V., Meinel, L., Hofmann, S., Malhotra, A., Volloch, V., Schwob, J., and Kaplan, D. (2004). "Bone morphogenetic protein-2 decorated fibroin films induce osteogenic differentiation of human bone marrow stromal cells." *J. Biomed Mats Res.*, 71A:528-537.

Karring, H., Thogersen, I., Klintworth, G., Moller-Pedersen, T., and Enghild, J. (2006). "The human cornea protcome; bioinformatic analyses indicate import of plasma proteins into the cornea." *Mol Vis*, 12:451-460.

Kawakita, T., Espana, E. M., He, H., Smiddy, R., Parel, J. M., Liu, C. Y., Tseng, S. C. (2006). "Preservation and expansion of the primate keratocyte phenotype by down-regulating TGF-beta signaling in a low-calcium, serum-free medium." *Invest Opthalmol Vis Sci*, 47(5):1918-1927.

Kim, B., Nikolovski, J., Bonadio, J., and Mooney, D. (1999). "Cyclic mechanical strain regulates the development of engineered smooth muscle tissue." *Nature Biotech*, 17:979-983.

Kim, J., Park, J., Kim, H., Wada, M., and Kaplan, D. (2005). "Three dimensional aqueous-derived biomaterial scaffolds from silk fibroin." *Biomaterials*, 26:2775-2785.

Kim, U., Park, J., Li, C., Jin, H., Valluzzi, R., and Kaplan, D. (2004). "Structure and Properties of Silk Hydrogels." *Biomacromolecules*, 5:786-792.

Li, F., Carlsson, D., Lohmann, C., Suuronen, E., Vascotto, S., Kobueh, K., Sheardown, H., Munger, R., Nakamura, M., and Griffith, M. (2003). "Cellular and nerve regeneration within a biosynthetic extracellular matrix for corneal transplantation." *PNAS*, 100(26):15346-15351.

Marchant. J., Hahn, R., Linsemayer, T., and Birk, D. (1996). "Reduction of type V collagen using a dominant-negative strategy alters the regulation of fibrillogensis and results in the loss of corneal-specific fibril morphology." *J Cell Biol* 135:1415-1426.

Marchant, J., Linsenmayer, T., and Gordon, M. (1991). "cDNA analysis predicts a cornea-specific collagen." *PNAS*, 88:1560-1564.

Marchant, J., Zhang, G., and Birk, D. (2002). "Association of type XII collagen with regions of increased stability and keratocyte density in the cornea." *Exp Eye Res*, 75:683-694.

Massia, S. P., Rao, S. S., and Hubbell, J. A. (1993). "Covalently immobilized larninin peptide Tyr-Ile-Gly-Ser-Arg (YIGSR) supports cell spreading and co-localization of the 67-kilodalton laminin receptor with alpha-actinin and vinculin." *J Biol Chem* 268(11):8053-8059.

Masur, S. K., H. S. Dewal, Dinh, T. T., Erenburg, I., Petridou, S. (1996). "Myofibroblasts differentiate from fibroblasts when plated at low density." *Proc Natl Acad Sci USA* 93(9): 4219-4223.

McGrath, K. (1998). "Protein-based Materials." Birkhauser.

McLaughlin, J., Linsenmayer, T., and Birk, D. (1989). "Type V collagen synthesis and deposition by chicken embryo fibroblasts in vitro." *J Cell Sci,* 94(Pt 2):371-379.

Meinel, L., Fajardo, R., Hofmann, S., Langer, R., Cherie, J., Snyder, B., Vunjak-Novakovic, G., and Kaplan, D. (2005a). "Silk implants for the healing of critical size bone defects." *Bone,* 37:688-698.

Meinel, L., Hofmann, S., Karageorgioue, V., Kirker-Heade, C., McCoole, J., Gronowiczf, G., Zichner, L., Langer, R., Vunjak-Novakovic, G., and Kaplan, D. (2005b). "The inflammatory responses to silk films in vitro and in vivo." *Biomaterials,* 26:147-155.

Mehta, J. S., C. E. Futter, Sandeman, S. R., Faragher, R. G., Hing, K. A., Tanner, K. E., B.0. (2005). "Hydroxyapatite promotes superior keratocyte adhesion and proliferation in comparison with current keratoprosthesis skirt materials." *Br J Ophthalmol* 89(10): 1356-1362.

Mimura, T., Yamagami, S., Yokoo, S., Usui, T., Tanaka, K., Hattori, S., Irie, S., Miyata, K., Araie, M., and Amano, S. (2004). "Cultured human corneal endothelial cell transplantation with a collagen sheet in a rabbit model." *Invest Opthalmol Vis Sci,* 45(9):2992-2997.

Minkowski, J., Bartels, S., Delori, F., Lee, S., Kenyon, K., and Neufeld, A. (1984). "Corneal endothelial function and structure following cryo-injury in the rabbit." *Invest Ophthamol Vis Sci,* 25(12):1416-1425.

Musselmann, K., B. Alexandrou, Kane, B., and Hassell, J. R. (2005). "Maintenance of the keratocyte phenotype during cell proliferation stimulated by insulin." *J Biol Chem* 280(38): 32634-32639.

Neidlinger-Wilke, C., Grood, E., Wang, J., Brand, R., and Claes, L. (2001). "Cell alignment is induced by cyclic changes in cell length: studies of cells grown in cyclically stretched substrates." *J Orthopaedic Res,* 19:286-293.

Nishida, K. (2003). "Tissue engineering of the cornea." *Cornea,* 22, suppl. 1:528-S34.

Nishida, K., Yamato, M., Hayashida, Y., Watanabe, K., Maeda, N., Watanabe, H., and Okano, T. (2004). "Functional Bioengineered corneal epithelial sheet grafts from corneal stem cells expanded ex vivo on a temperature-responsive cell culture surface." *Transplantation,* 77(3): 379-385.

Nishiyama, T., McDonough, A., Bruns, R., and Burgeson, R. (1994). "Type XII and XIV collagens mediate interactions between banded collagen fibers in vitro and may modulate extracellular matrix deformability." *J Biol Chem,* 269: 28193-28199.

Ottino, P., J. He, Axelrad, T. W., and Bazan, H. E. (2005). "PAF-induced Turin and MT1-MMP expression is independent of MMP-2 activation in corneal myofibroblasts." *Invest Ophthalmol Vis Sei* 46(2): 487-96.

Panilaitis, B., Altman, G., Chen, J., J M, H., Karageorgiou, V., and Kaplan, D. (2003). "Macrophage responses to silk." *Biomaterials,* 24:3079-3085.

Panjwani, N. (1997). "Cornea and sclera." chapter 2, pages 16-51. Chapman & Hall.

Park, J. (2004). "Structure and properties of water annealed silk fibroin films." Master's thesis, Tufts University.

Petroll, W., Boettcher, K., Barry, P., Cavanagh, H., and Jester, J. (1995). "Quantitative assessment of anteroposterior keratocyte density in the normal rabbit cornea." *Cornea,* 14(1):3-9.

Poole, C., Brookes, N., and Clover, G. (1993). "Keratocyte networks visualised in the living cornea using vital dyes." *J Cell Science,* 106:685-692.

Raymond, G., Jumblatt, M., Bartels, S., and Neufeld, A. (1986). "Rabbit Corneal Endothelial Cells in Vitro: Effects of EGF." *Invest Ophthalmol Vis Sci,* 27:474-479.

Ronge, L. (2001). "LASIK shatter assumptions." *American Academy of Ophthalmology: Eye Net,* August:1.

Shimizu, T., Yamato, M., Kikuchi, A., and Okano, T. (2003). "Cell sheet engineering for myocardial tissue reconstruction." *Biomaterials,* 24:2309-2316.

Shyy, J. and Chien, S. (1997). "Role of integrins in cellular responses to mechanical stress and adhesion." *Curr Opin Cell Biol,* 9:707-713.

Sofia, S., McCarthy, M., Gronowicz, G., and Kaplan, D. (2001). "Functionalized silk-based biomaterials for bone formation." *J Biomed Mater Res,* 54(1):139-148.

Sokolnicki, A. M., Fisher, R. J., Harrah, T. P. & Kaplan, D. L. (2006) "Permeability of bacterial cellulose membranes." *J Membr Sci* 272 15.

Stark, H., Szabowski, A., Fusenig, N.; and Maas-Szabowski, N. (2004). "Organotypic cocultures as skin equivalents: A complex and sophisticated in vitro system." *Biol. Proced. Online,* 6(1):55-60.

Steele, C. (1999). "Corneal wound healing: a review." *Optometry Today,* 9:28-32.

Sung, H., Meredith, C., Johnson, C., and Galis, Z. (2004). "The effect of scaffold degradation rate on three-dimensional cell growth and angiogenesis." *Biomaterials,* 25:5735-5742.

Trachslin, J., Koch, M., and Chiquet, M. (1999). "Rapid and reversible regulation of collagen XII expression by changes in tensile stress." *Exp Cell Res,* 247:320-328.

Walboomers, X. F., Monaghan, W., Curtis, A. S. G., and Jansen, J. A. (1999). "Attachment of fibroblasts on smooth and microgrooved polystyrene." *J Biomed Mater Res,* 46:212-220.

Wang, X., Kim, H., Xu, P., Matsumoto, A., and Kaplan, D. (2005). "Biomaterial coating by stepwise deposition of silk fibroin." *Langmuir,* 21(24):11335-11341.

Wang, X., Blasioli, D., Kim, H., Kim H., and Kaplan, D. (2006). "Cartilage tissue engineering with silk scaffolds and human articular chondrocytes." *Biomaterials,* 27:4434-4442.

Wessel, H., Anderson, S., Fit; D., Halvas, E., Hempel, J., and SundarRaj, N. (1997). "Type XII collagen contributes to diversities in human corneal and limbal extracellular matrices." *Invest Ophthalmol Vis Sci,* 38:2408-2422.

Wilson, D., Valluzzi, R., and Kaplan, D. (2000). "Conformational transitions in model silk peptides." *Biophysical J.,* 78:2690-2701.

Wilson, S. E., M. Netto, Ambrosio, R. Jr. (2003). "Conical cells: chatty in development, homeostasis, wound healing, and disease." *Am J Ophthalmol* 136(3): 530-6.

Yang, J., Yamata, M., Kohno, C., and Nishimoto, A. (2005). "Cell sheet engineering: Recreating tissues without biodegradable scaffolds." *Biomaterials,* 26:6415-6422.

Biological efficacy of silk fibroin nanofiber membranes for guided bone regeneration. Kim, K-H.; Jeong, Lim; Park, Ho-Nam; Shin, Seung-Yun; Park, Won-Ho; Lee. Sang-Chul; Kim, Tae-Il; Park, Yoon-Jeong; Seol, Yang-Jo; Lee, Yong-Moo: Ku, Young: Rhyu, In-Chul; Han, Soo-Boo; Chung, Chong-Pyoung. Journal of Biotechnology (2005), 120(3), 327-339.

Structural and mechanical characteristics of silk fibroin and chitosan blend scaffolds for tissue regeneration. Gobin, Andrea S.; Froude, Victoria E.; Mathur, Anshu B. Journal of Biomedical Materials Research, Part A (2005), 74A(3), 465-473.

The healing of confined critical size cancellous defects in the presence of silk fibroin hydrogel. Fini. M.; Motta. A.; Torricelli, P.; Giavaresi, G.; Nicoli Aldini, N.; Tschon, M.; Giardina, R.; Migliaresi. C. Biomaterials (2005), 26(17). 3527-3536.

De novo engineering of reticular connective tissue in vivo by silk fibroin nonwoven materials. Dal Pra, Ilaria: Freddi, Giuliano; Minic, Jasminka; Chiarini, Anna; Armato, Ubaldo. Biomaterials (2005). 26(14), 1987-1999.

Endothelialization of a non-woven silk fibroin net for use in tissue engineering: growth and gene regulation of human endothelial cells. Unger, R. E.; Peters, K.; Wolf, M.; Motta, A.; Migliaresi, C.; Kirkpatrick. C. J. Biomaterials (2004), 25(21). 5 137-5146.

Clotting times and tensile properties of insoluble silk fibroin films containing heparin. Lv, Qiang: Cao, Chuanbao; Zhu, Hesun. Polymer International (2005). 54(7). 1076-1081.

Outgrowth endothelial cells isolated and expanded from human peripheral blood progenitor cells as a potential source of autologous cells for endothelialization of silk fibroin biomaterials. Fuchs, Sabine; Motta, Antonella; Migliaresi, Claudio; Kirkpatrick, Charles James. Biomaterials (2006), 27(31), 5399-5408.

Biomaterials. 2007 Mar., 28(9): 1643-52, "Biocompatibility evaluation of silk fibroin with peripheral nerve tissues and cells in vitro" Yang Y, Chen X, Ding F, Zhang P, Liu I, Gu X.

We claim:

1. A lamellae tissue layer, comprising a grooved silk fibroin substrate comprising tissue-specific cells aligned thereon,
    wherein the thickness of the substrate ranges from 10 nm to 1 mm, the grove width is at least 125 nm, and the groove thickness depth is at least 100 nm, such that the grooves in the substrate induce cell and extracellular matrix (ECM) alignment when said cells are cultured thereon; and
    wherein the cells are selected from the group consisting of stem cells, fibroblasts, endothelial cells, epithelial cells, adipose cells capable of generating ECM on the substrate, and combinations thereof.

2. The lamellae tissue layer of claim 1, wherein the tissue-specific cells deposit extracellular matrix on the substrate.

3. A tissue-engineered organ comprising a multitude of lamellae tissue layers, each layer comprising a grooved silk fibroin substrate of claim 2.

4. The tissue-engineered organ of claim 3, wherein the organ comprises micropores,
    wherein spacing between the micropores is 50 μm to 100 μm and,
    wherein an average diameter of the micropores ranges from 500 nm to 100 μm.

5. The tissue-engineered organ of claim 4, wherein the micropores are created through the use of poly(ethylene oxide) phase separation chemistry, laser ablation techniques, or a combination thereof.

6. The tissue-engineered organ of claim 3, wherein the organ is any tissue that can be formed by the assembly of the silk fibroin substrates with cultured cells and deposited extra cellular matrix.

7. The tissue-engineered organ of claim 3, wherein the organ is a cornea.

8. The tissue-engineered organ of claim 3, wherein the organ is optically clear, non-immunogenic and biocompatible.

9. The tissue-engineered organ of claim 3, wherein the organ comprises an endothelial cell sheet on the bottom of the lamellae tissue layers and an epithelial cell sheet on the top of the lamellae tissue layers.

10. The tissue-engineered organ of claim 3, wherein edges of the tissue engineered organ are sealed.

11. The tissue-engineered organ of claim 3, comprising:
    at least two lamellae tissue layers, each layer comprising a grooved silk fibroin substrate comprising fibroblast cells aligned thereon, such that the grooves in the substrate induce cell and extracellular matrix alignment when said cells are cultured thereon,
    an endothelial cell sheet on the bottom of the lamellae tissue layers, and
    an epithelial cell sheet on the top of the lamellae tissue layers.

12. The tissue-engineered organ of claim 3, wherein the organ is a cornea comprising:
    an endothelial cell sheet on the bottom of the lamellae tissue layers, and
    an epithelial cell sheet on the top of the lamellae tissue layers, wherein a thickness of the grooved silk fibroin substrate ranges from at least about 100 nm to about 1 mm, a groove width is as least 125 nm, and a groove thickness depth is at least 100 nm, and wherein the cornea comprises micropores with a spacing of 50 μm to 100 μm.

13. The tissue engineered organ of claim 4, wherein the average diameter of the micropores is 1 μm to 10 μm.

* * * * *